US009642682B2

(12) United States Patent
Kato

(10) Patent No.: US 9,642,682 B2
(45) Date of Patent: May 9, 2017

(54) METHOD FOR MANUFACTURING AN INTERDENTAL CLEANING TOOL AND THE INTERDENTAL CLEANING TOOL

(71) Applicant: Keisuke Kato, Takatsuki (JP)

(72) Inventor: Keisuke Kato, Takatsuki (JP)

(73) Assignee: SUNSTAR SUISSE SA, Etoy (CH)

( * ) Notice: Subject to any disclaimer, the term of this patent is extended or adjusted under 35 U.S.C. 154(b) by 0 days.

(21) Appl. No.: 14/402,522

(22) PCT Filed: May 24, 2013

(86) PCT No.: PCT/JP2013/065127
§ 371 (c)(1),
(2) Date: Nov. 20, 2014

(87) PCT Pub. No.: WO2013/176297
PCT Pub. Date: Nov. 28, 2013

(65) Prior Publication Data
US 2015/0114428 A1 Apr. 30, 2015

(30) Foreign Application Priority Data

May 24, 2012 (JP) .................................. 2012-118916
Mar. 5, 2013 (JP) .................................. 2013-042925

(51) Int. Cl.
*B29C 45/14* (2006.01)
*A61C 15/02* (2006.01)
(Continued)

(52) U.S. Cl.
CPC .......... *A61C 15/02* (2013.01); *A46B 15/0093* (2013.01); *A46D 3/00* (2013.01);
(Continued)

(58) Field of Classification Search
CPC .............. A61C 15/00; A46B 2200/108; B29C 45/14065; B29C 45/14073; B29C 45/0046; B29C 2045/0049
(Continued)

(56) References Cited

U.S. PATENT DOCUMENTS 6,085,761 A * 7/2000 Inaba ................. A61C 15/02
132/329
6,158,444 A * 12/2000 Weihrauch ............. A61C 15/02
132/200
(Continued)

FOREIGN PATENT DOCUMENTS

DE 4330323 A1 3/1995
DE 19642431 A1 4/1998
(Continued)

OTHER PUBLICATIONS

International Search Report for International Application No. PCT/JP2013/065127 dated Jun. 25, 2013.
(Continued)

*Primary Examiner* — Atul P. Khare
(74) *Attorney, Agent, or Firm* — Kratz, Quintos & Hanson, LLP

(57) ABSTRACT

To provide a method for manufacturing an interdental cleaning tool that can prevent deformation of a core base at molding of a cleaning flexible part using an elastomer material, thereby effectively preventing occurrence of molding failure of the cleaning flexible part.
The method in the present invention includes: a base part molding step of providing first metal molds 30 and 31 for molding base parts with a plurality of first molding spaces 32 aligned in parallel and including core base molding sections 32a and handle base molding sections 32b, providing the first metal molds 30 and 31 with connection part molding sections 35 to communicate with the adjacent handle base
(Continued)

molding sections 32b, and supplying a synthetic resin material with a fiber material at a time to the plurality of first molding spaces 32 from gates 34 to form a plurality of base parts at a time; and a flexible part molding step of setting the core bases of the base parts into second metal molds, holding the core bases at two or more longitudinal portions by a plurality of pairs of hold pins in the second metal molds, each pair including two pins, and charging an elastomer material into the cleaning flexible part molding spaces.

11 Claims, 16 Drawing Sheets

(51) Int. Cl.
*A46B 15/00* (2006.01)
*A46D 3/00* (2006.01)
*B29C 45/26* (2006.01)
*B29C 45/00* (2006.01)
*B29K 23/00* (2006.01)
*B29K 67/00* (2006.01)
*B29K 77/00* (2006.01)
*B29L 31/42* (2006.01)

(52) U.S. Cl.
CPC ...... *B29C 45/0046* (2013.01); *B29C 45/0081* (2013.01); *B29C 45/14065* (2013.01); *B29C 45/14073* (2013.01); *B29C 45/14426* (2013.01); *B29C 45/2669* (2013.01); *A46B 2200/108* (2013.01); *B29C 2045/0049* (2013.01); *B29K 2023/12* (2013.01); *B29K 2067/006* (2013.01); *B29K 2077/00* (2013.01); *B29L 2031/425* (2013.01)

(58) Field of Classification Search
USPC .................. 264/275, 277, 278, 328.8, 328.12
See application file for complete search history.

(56) References Cited

U.S. PATENT DOCUMENTS

| | | | |
|---|---|---|---|
| 6,652,796 B1* | 11/2003 | Moriwaki | C08J 3/201 264/328.1 |
| 2009/0230756 A1* | 9/2009 | Crossman | A46B 5/02 300/21 |
| 2010/0024839 A1* | 2/2010 | Kalbfeld | A46B 1/00 132/329 |

FOREIGN PATENT DOCUMENTS

| | | |
|---|---|---|
| EP | 2100570 A1 | 9/2009 |
| JP | H11-254475 | 9/1999 |
| JP | 3002668 B1 | 1/2000 |
| JP | 2011-506514 A1 | 5/2001 |
| JP | 2002137248 A * | 5/2002 |
| JP | 2002-187160 A1 | 7/2002 |
| JP | 2004209242 A * | 7/2004 |
| JP | 2008093957 A * | 4/2008 |
| JP | 4236571 B2 | 3/2009 |
| JP | WO 2009150964 A1 * | 12/2009 ............... A46D 5/00 |
| JP | 2011-529729 A1 | 12/2011 |
| WO | WO 98/16169 A1 | 4/1998 |
| WO | WO 2010/014623 A1 | 2/2010 |

OTHER PUBLICATIONS

DE 112013002612.0: Office Action issued Oct. 6, 2015—English language translation only.
EP 13793707.4: Extended European Search mailed Dec. 11, 2015.

* cited by examiner

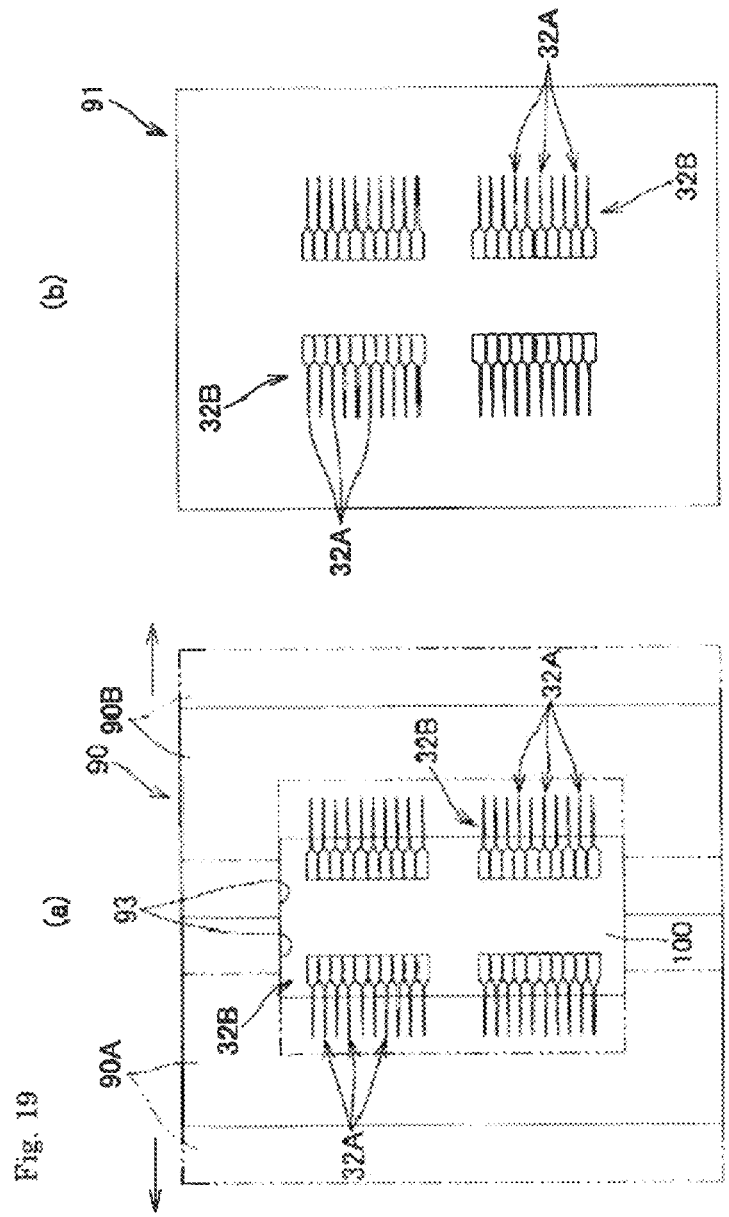

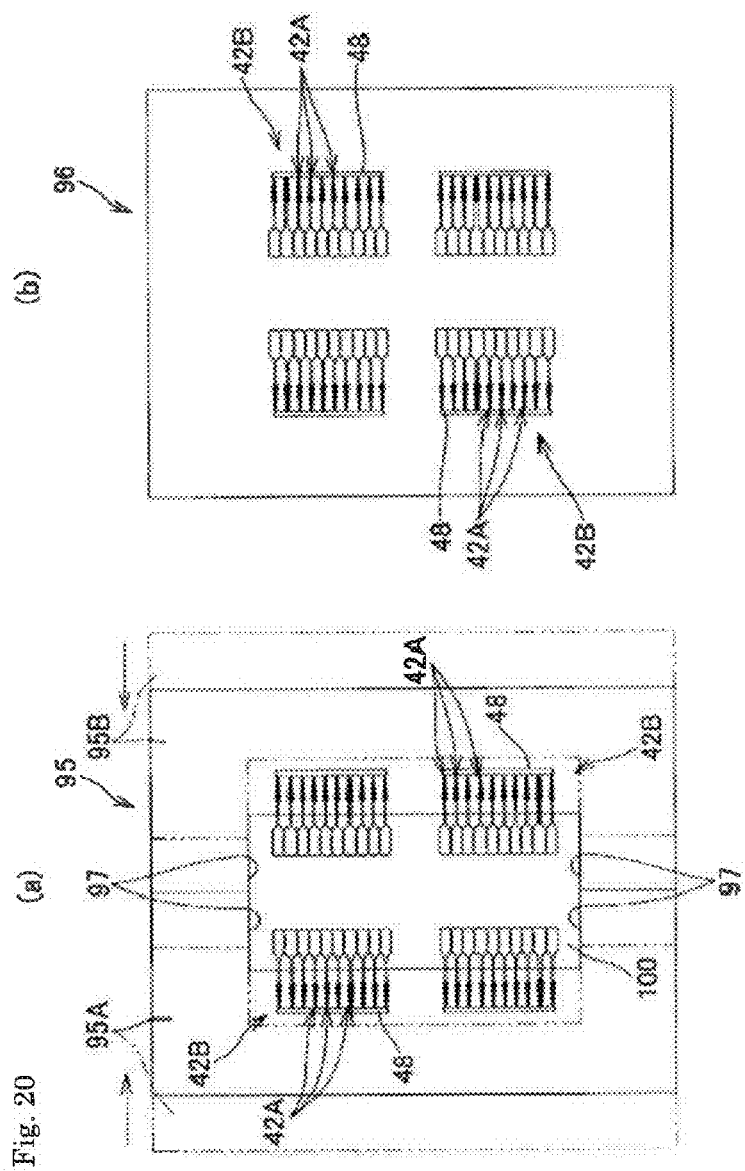

US 9,642,682 B2

METHOD FOR MANUFACTURING AN INTERDENTAL CLEANING TOOL AND THE INTERDENTAL CLEANING TOOL

TECHNICAL FIELD

The present invention relates to a method for manufacturing an interdental cleaning tool having a cleaning part covered by an elastomer, and the interdental cleaning tool.

BACKGROUND

There has been commercialized an interdental cleaning tool including: a base part made of a synthetic resin, the base part having a handle base and an elongated shaft-like core base provided at a leading end of the handle base; and a flexible part made of an elastomer, the flexible part having at least a cleaning flexible part covering the core base, the handle base constituting a handle part, and the core base and the cleaning flexible part constituting an interdental cleaning part (for example, refer to Patent Documents to 3).

In a widely used method for manufacturing the interdental cleaning tool, a synthetic resin material is charged into a first molding space of a first metal mold to produce the base part, the base part molded by the first metal mold is set into a second molding space of a second metal mold, an elastomer material is charged into the second molding space to mold a flexible part, thereby obtaining the interdental cleaning tool. In general, to obtain a plurality of interdental cleaning tools, a plurality of first molding spaces is provided in the first metal mold, and the same number of second molding spaces as the first molding spaces are provided in the second metal mold. At manufacture of the interdental cleaning tools, the synthetic resin material is supplied to the plurality of first molding spaces to produce a plurality of base parts connected to each other by runner parts at a time, a primary molded article formed by the plurality of base parts connected to each other by the runner parts is set into the second molding spaces of the second metal mold, and the elastomer material is charged into the plurality of second molding spaces, thereby molding the plurality of interdental cleaning tools at a time.

To simplify a metal old structure as much as possible, in general, at charging of the elastomer material into the second molding spaces, gates are disposed at leading end sides of the interdental cleaning tools in the second molding spaces, and the elastomer material is charged from leading end sides to base end sides of the core bases of the base parts charged in the second molding spaces. In addition, the elastomer material is relatively high in viscosity. Thus, at molding of the cleaning flexible parts in the second molding spaces, if the elastomer material is charged from the base sides to the leading end sides of the core base, charging failure may occur at the leading ends of the cleaning flexible parts. Partly due to this, the elastomer material is generally charged from the leading end sides to the base end sides of the core bases to prevent molding failure at the leading ends of the cleaning flexible parts.

CITATION LIST

Patent Literatures

Patent Document 1: Japanese Patent No. 4236571
Patent Document 2: Japanese Patent No. 3002668
Patent Document 3: Japanese Unexamined Patent Application Publication (Translation of PCT Application) No. 2001-506514

SUMMARY OF INVENTION

Technical Problem

However, when the elastomer material is charged into the second molding spaces from the leading ends to the base ends of the core bases as described above, opening areas of the gates cannot be widened and thus an injection pressure of the elastomer becomes high and is prone to vary around the core bases in the vicinity of the gates. This causes a problem of molding failure that the core bases are curved toward the side with a lower injection pressure and are exposed to the outside. In addition, the elastomer material is heated to near a melting temperature of the core bases for enhancement of adhesiveness to the core bases. This causes a problem that the core bases are softened and prone to be deformed by heat from the elastomer material, and thus may be deformed even with slight variations in injection pressure.

An object of the present invention is to provide a method for manufacturing an interdental cleaning tool that can prevent deformation of a core base at molding of a cleaning flexible part using an elastomer material, thereby effectively preventing occurrence of molding failure of the cleaning flexible part, and the interdental cleaning tool.

Solution to Problem

A method for manufacturing an interdental cleaning tool according to the present invention is a method for manufacturing an interdental cleaning tool including: a base part made of a synthetic resin, the base part having a handle base and an elongated shaft-like core base connected to a leading end of the handle base; and a flexible part made of an elastomer and covering at least a portion of the base part, the flexible part having at least a cleaning flexible part covering the core base, the handle base constituting a handle part, and the core base and the cleaning flexible part constituting an interdental cleaning part, wherein the method for manufacturing an interdental cleaning tool includes: a base part molding step of providing a metal mold for molding the base part with a plurality of first molding spaces aligned in parallel and including core base molding sections and handle base molding sections; providing the metal mold with connection part molding sections to communicate with the adjacent handle base molding sections; supplying a synthetic resin material with a fiber material at a time to the plurality of first molding spaces from gates opened to the first molding spaces at base end sides of the first molding spaces opposite to the core base molding sections; and molding a plurality of base parts at a time such that the base parts are connected to each other in parallel by connection parts molded at the connection part molding sections, and a flexible part molding step of: transferring the plurality of base parts molded and connected to each other at the base part molding step, to a metal mold for molding the flexible part; setting at least portions of the core bases of the base parts into a plurality of second molding spaces in the metal mold; holding the core bases at two or more longitudinal portions including the leading ends and base ends of the core bases, at almost centers of the each cleaning flexible part molding sections, using at least two pairs of hold pins, each pair including two pins that are opposed to each other and protruded within the each cleaning flexible part molding sections so as to be approximately orthogonal to matching surfaces of the metal mold; and charging an elastomer material into the second molding spaces such that the elastomer material is supplied from the leading end sides to base end sides of the cleaning flexible part molding sections.

In the manufacturing method, first, at the base part molding step, the synthetic resin material with the fiber material is supplied at a time to the plurality of first molding spaces from the gates at the base end sides of the first molding spaces to mold the plurality of base parts connected to each other by the connection parts. Then, at the flexible part molding step, the plurality of base parts molded at the base part molding step and connected to each other by the connection parts, is transferred to the metal mold for molding the flexible parts; at least portions of the core bases of the base parts (including at least portions of the core bases covered by the cleaning flexible parts) are set into the second molding spaces; the portions of the core bases are held at almost centers of the cleaning flexible part molding sections so as to be positioned at centers of the cleaning flexible part molding sections, by the plurality of hold pins; and the elastomer material is charged into the cleaning flexible part molding sections from the leading end sides to base end sides thereof, thereby manufacturing the interdental cleaning tools in which the flexible parts are molded integrally with the base parts.

As in the foregoing, according to the manufacturing method, the synthetic resin material with the fiber material is supplied at a time to the plurality of first molding spaces via the gates at the base ends of the first molding spaces. Accordingly, the fiber material is oriented along the length of the first molding spaces, that is, the length of the base parts. This makes it possible to improve in particular the core bases in bending strength and buckling strength along the axial direction, and effectively prevent folding and buckling of the core bases at use of the interdental cleaning tools. The fiber material also improves the base parts in dimension stability and strength rigidity to prevent deformation of the core bases. This makes it possible to prevent that at least portions of the core bases in the base parts are defectively charged into the second molding spaces. The fiber material also raises the heat distortion temperature of the core bases, and thus it is possible to effectively prevent softening and deformation of the core bases due to heat generated from the elastomer material at molding of the cleaning flexible parts. The fiber material also raises the strength rigidity of the core bases, and thus it is possible to prevent deformation of the core bases under an injection pressure of the elastomer material. Accordingly, it is possible to prevent the core bases from being deformed at molding of the cleaning flexible parts, and thus it is possible to prevent the molding failure of the cleaning flexible parts in a further effective manner.

The addition of the fiber material allows the plurality of base parts to be connected by the connection parts at an appropriate strength. This makes it possible to transfer the plurality of base parts molded at the base part molding step at a time into the second molding spaces at the flexible part molding step, thereby smoothly molding a plurality of interdental cleaning tools at a time. In addition, even if the manufactured interdental cleaning tools are packaged in a state of being connected by the connection parts, it is possible to prevent that the interdental cleaning tools connected by the connection parts are separated from each other due to vibrations generated in the processes of packaging or distribution/sale. Further, for use, the interdental cleaning tools can be separated on the connection parts by hand in a relatively easy manner. Specifically, if no fiber material is added, the use of polypropylene (PP) as the synthetic resin material, for example, makes it hard to separate the interdental cleaning tools on the connection parts due to deformation of the connection parts. Meanwhile, the use of polybutylene terephthalate (PBT) as the synthetic resin material makes the connection parts prone to be broken, which causes a problem that the plurality of base parts molded at the base part molding step cannot be transferred at a time to the second molding spaces or the plurality of manufactured interdental cleaning tools connected by the connection parts is unfavorably separated from each other in the processes of packaging or distribution/sale. In addition, the fiber material added to the synthetic resin material is also oriented along the length of the first molding spaces, that is, the length of the interdental cleaning tools, around boundary sections between the handle base molding sections and the connection part molding sections. Accordingly, the interdental cleaning tools molded in parallel can be properly cut and separated by bending double the adjacent interdental cleaning tools on the connection parts and breaking off the connection parts without significant deformation of surrounding parts of the connection parts. However, it is necessary to set the connection strength between the connection parts and the base parts such that these parts are not easily separated from each other due to vibrations generated when the base parts are transferred from the first molding spaces to the second molding spaces or when the manufactured interdental cleaning tools are in the processes of packaging or distribution/sale or the like.

The elastomer material is charged from the leading end sides to the base end sides of the core bases to mold the cleaning flexible parts. This makes it possible to mold the plurality of interdental cleaning tools at a time without complicating the structure of the metal mold for molding the flexible parts. In addition, the core bases are held at two or more longitudinal portions including the leading ends and base ends of the core bases, by at least two pairs of hold pins each of which includes two hold pins opposed to each other. The plurality of opposed pins are protruded within the cleaning flexible part molding sections so as to be approximately orthogonal to matching surfaces of the metal mold for molding the flexible parts, that is, protruded in a direction of opening and closing of the metal mold for molding the flexible parts. Accordingly, as compared to conventional cases in which the core bases are held by three or more hold pins at the same positions in a circumferential section along the length of the core bases, it is possible to simplify the structure of the metal mold for molding the flexible parts, and reduce difficulty of flowing of the elastomer material in the cleaning tool molding spaces (hereinafter, referred to as flow resistance). It is also possible to suppress influence of Karman vortex generated near the hold pins at charging of the elastomer. In addition, the elastomer material is charged from the leading end sides of the core bases in which the elastomer material is most difficult to flow, which makes it possible to provide sufficient moldability of the leading ends of the cleaning flexible parts.

In a preferred embodiment, the connection part molding sections are elongated along length of the handle base molding sections and are made thinner with increasing proximity to a first boundary section of two boundary sections between the connection part molding section and the handle base molding sections on both sides of the connection part molding section. According to the foregoing configuration, the synthetic resin material supplied to the handle base molding sections can easily enter the connection part molding sections from the second boundary section side. Even if the synthetic resin material reaches simultaneously the both boundary sections, the synthetic resin material supplied to the adjacent handle base molding sections joins near the first boundary sections, and thus the molded base parts can be easily cut and separated at positions corresponding to the first boundary sections. In addition, the fiber material added to the synthetic resin material is prone to be oriented along the length of the handle base molding sections around the first boundary sections of the connection part molding sections. This also allows the base parts to be easily cut and separated at positions corresponding to the first boundary sections. Accordingly, the plurality of interdental cleaning tools molded at a time can be easily cut and separated in sequence from the outside.

In a preferred embodiment, of the two boundary sections between the connection part molding section and the ha idle base molding section on the both sides of the connection part molding section, the length of the first boundary section along the length of the handle base molding section is set shorter than the length of the second boundary section. According to the foregoing configuration, the synthetic resin material supplied to the handle base molding section can enter the connection part molding sections more smoothly from the second boundary section side. This makes it possible to allow the synthetic resin material supplied to the adjacent handle base molding parts to join near the first boundary sections in a further effective manner. In addition, it is possible to allow the fiber material to be oriented further properly along the length of the handle bases around the first boundary sections. Accordingly, the interdental cleaning tools can be cut and separated in a further easy manner at positions corresponding to the first boundary sections.

In a preferred embodiment, two or more connection part molding sections are arranged at intervals along the length of the handle base molding section. Only one connection part molding section can be arranged in the middle of the handle base molding section along the length. However, if the number of the connection part molded by the connection part molding section is one, it is not possible to provide sufficient connection strength of the adjacent base parts. Thus, after molding of the interdental cleaning tools, the connection parts may be broken to let the interdental cleaning tools fall apart at opening of the molds, or the connection parts may be folded and deformed. This readily causes charging failure of the base parts into proper positions of the second molding spaces, thereby resulting in molding failure of interdental cleaning flexible parts. Accordingly, two or more connection part molding sections are preferably provided between a pair of adjacent base parts. In addition, if the length of the connection parts is too large along the length of the base parts, when the interdental cleaning tools are cut and separated, the connection parts may have sharp-edge corners at both ends of the cut surfaces. Accordingly, two or more short connection part molding sections are preferably arranged at intervals along the length of the handle base molding sections.

Preferably, the fiber material uses glass fiber, and the combination ratio of the glass fiber to the synthetic resin material is set at 12 weight % or more and 35 weight % or less. Specifically, if the combination ratio of the glass fiber as the fiber material is less than 12 weight %, the cleaning part is prone to be bent and hard to insert into between adjacent teeth of pore structure. If the combination ratio exceeds 35 weight % the cleaning part is prone to be broken and may injure inside the mouth of the user, or broken pieces may be accidentally swallowed by the user. Accordingly, the preferred combination ratio is set between 12 weight % or more and 35 weight % or less.

In a preferred embodiment, the synthetic resin material is polypropylene (PP), polybutylene terephthalate (PBT), or polyamide. Preferably in particular, polypropylene is low in molding temperature and can shorten a cycle time and improve productivity, and imposes less heat load on molding equipment. If polypropylene (PP) is used as the synthetic resin material, the combination ratio of the fiber material is preferably set at 15 weight % or more and 35 weight % or less. If polybutylene terephthalate (PBT) is used, the combination ratio is preferably set at 12 weight % or more and 35 weight % or less.

In a preferred embodiment, a pair of hold pins holding the leading end of the core base has a cross section area of a portion in contact with the core base set at 0.03 to 0.3 mm$^2$, the pair of hold pins is arranged at positions where leading ends of the pins are in contact with the core base corresponding to a range of 3 mm from the leading end to base end of the cleaning flexible part molding section, a pair of hold pins holding the base end of the core base has a cross section area of a portion in contact with the core base set at 0.1 to 1.1 mm$^2$, and the pair of hold pins is arranged at positions where leading ends of the pins are in contact with the core base corresponding to a range of 6 mm from the base end to leading end of the cleaning flexible part molding section. In this embodiment, it is possible to hold stably the core base at the center of the cleaning flexible part molding section while minimizing a flow resistance to the elastomer material, and suppress influence of Karman vortex generated at molding of the flexible part on the molded body. Accordingly, even with certain variations in injection pressure, it is possible to suppress deformation of the core base and prevent molding failure due to deformation of the core base.

As far as the hold pins meet the foregoing conditions, the hold pins are only required to be protruded in the cleaning flexible part molding sections so as to be approximately orthogonal to opposing surfaces, that is, the matching surfaces of the metal mold for molding the flexible parts. In a more preferred mode, the core base is held by the two hold pins at the same positions in a circumferential section and a surrounding section thereof along the length of the core base. In a further preferred mode, after the two hold pins are arranged at the same positions in a circumferential section along the length of the core base, one of the two hold pins is displaced at a leading end portion thereof by a distance shorter than the longitudinal length of the cleaning flexible part molding section, in the longitudinal direction of the cleaning flexible part molding section. When the two opposed hold pins are thus displaced along the length of the cleaning flexible molding section, the core base is held between the hold pins by a substantially wider area. Accordingly, the core base can be held more firmly.

In a preferred embodiment, the cross section area of the hold pins is set larger with increasing proximity to the base side of the cleaning flexible part molding section. The cleaning flexible part molding section is larger in path area with increasing proximity to the base end side. According to this, when the cross section area of the hold pins is set larger with increasing proximity to the base side of the cleaning flexible part molding section, it is possible to minimize a flow resistance to the elastomer material at the leading end of the cleaning flexible part molding section, and further suppress influence of Karman vortex generated near the hold pins on the molded body and the hold pins. Accordingly, it is possible to hold the core base more reliably and prevent charging failure of the elastomer material into the cleaning flexible part molding section. In addition, there is no particular limitation on the cross section shape of the hold pins. For example, the cross section of the hold pins may have a polygonal shape such as circular, oval, triangular, square, or any other shape. Of the foregoing shapes, preferred shapes are circle, oval, square, and teardrop (drop shape), from the viewpoint of further suppressing influence of Karman vortex generated near each of the hold pins on the molded body and the hold pins.

The hold pins can be provided to freely appear at the cleaning flexible part molding section. The hold pins may be provided in a fixed manner at the metal mold for molding the flexible parts. In this case, however, when the base parts molded by the metal mold for molding the base parts are set into the metal mold for molding the flexible parts, the core bases contact the hold pins, which is prone to cause charging failure of the core bases into the metal mold for molding the flexible parts. Thus, preferably as in the present invention, the hold pins are provided to freely appear at the cleaning flexible part molding section, and the hold pins are immersed into the metal mold when the core bases are charged into the cleaning flexible part molding sections in the second molding spaces, and the core bases are charged into the cleaning flexible part molding sections with no protrusion of the hold pins, and then the mold is closed and the hold pins are protruded. Accordingly, it is possible to hold the core bases at proper positions and prevent charging failure of the core bases into the metal mold for molding the flexible parts.

In a preferred embodiment, the synthetic resin material for forming the base parts and the elastomer material for forming the flexible parts are compatible with each other. In this case, it is possible to effectively prevent the flexible parts from separating from the base parts, thereby realizing durable interdental cleaning tools.

In a preferred embodiment, the elastomer material is a styrene-based elastomer material that has a high flowability even at a low degree of hardness and a favorable adhesion to synthetic resin, as compared to other elastomers, for example, olefin-based elastomers. More specifically, the elastomer material has a shore A value of 5 to 70, preferably 10 to 50, more preferably 20 to 50, and most preferably 30 to 40.

The interdental cleaning tool according to the present invention includes: a base part made of a synthetic resin, the base part having a handle base and an elongated shaft-like core base connected to a leading end of the handle base; and a flexible part made of an elastomer and covering at least a portion of the base part, the flexible part having at least a cleaning flexible part covering the core base, the handle base and, in some cases, the flexible part constituting a handle part, and the core base and the cleaning flexible part constituting an interdental cleaning part, wherein a plurality of interdental cleaning tools is aligned in parallel, connection parts for connecting the adjacent interdental cleaning tools are provided across the adjacent handle bases so as to be integral with the handle bases, the base parts are made of a synthetic resin material with a fiber material, the fiber material is oriented along length of the base part, and at least around a first boundary part of two boundary parts between the connection part and the handle bases on both sides of the connection part, the fiber material is oriented along length of the base part such that the adjacent interdental cleaning parts can be cut and separated at the first boundary part.

In the interdental cleaning tools, the fiber material is oriented along the length of the base parts. This makes it possible to improve the core base parts in bending strength and buckling strength along the axial direction, and effectively prevent folding and buckling of the core bases at use of the interdental cleaning tools. The fiber material also improves the base parts in dimension stability and strength rigidity, thereby to prevent deformation of the base parts and mold the cleaning flexible parts with accuracy with respect to the base parts. This makes it possible to realize high-quality interdental cleaning tools with accuracy. Further, connecting a plurality of interdental cleaning tools in parallel improves the interdental cleaning tools moldability and ease of packaging. In addition, at least around the first boundary part of the two boundary parts between the connection part and the handle base, the fiber material is oriented along the length of the handle base. This allows the connection parts to be broken off without deformation of surrounding parts of the connection parts. Accordingly; the interdental cleaning tools connected in parallel can be properly cut and separated at the first boundary parts.

In a preferred embodiment, the connection parts are elongated along length of the handle bases and are made thinner with increasing proximity to the first boundary parts. According to the foregoing configuration, as described above in detail on the manufacturing method, the synthetic resin material supplied to the adjacent handle base molding sections joins at the first boundary parts of the connection parts. In addition, the fiber material added to the synthetic resin material is prone to be oriented along the length of the handle bases at the first boundary parts. Accordingly, when using the interdental cleaning tools, the interdental cleaning tools can be easily cut and separated at the first boundary parts without large deformation of the surrounding parts of the first boundary parts.

In a preferred embodiment, the length of the first boundary part along the length of the handle base is set shorter than the length of the second boundary part. According to the foregoing configuration, connection strength between the connection part and the handle base at the first boundary part can be smaller than connection strength between the connection part and the handle base at the second boundary part. This makes the interdental cleaning tools to be cut and separated at the first boundary part in a further easy and smooth manner.

In a preferred embodiment, two or more connection parts are arranged at intervals along the length of the handle base. Only one connection part can be arranged in the middle of the handle base along the length. In this case, however, it is not possible to provide sufficient connection strength of the adjacent base parts. Thus, after molding of the interdental cleaning tools, the connection parts may be broken to let the interdental cleaning tools fall apart at opening of the molds, or the connection parts may be folded and deformed, thereby resulting in molding failure. Accordingly; two or more connection parts are preferably provided. In addition, if the length of the connection parts is too large along the length of the base parts, when the interdental cleaning tools are cut and separated, the connection parts may have sharp-edge corners at both ends of the cut surfaces. Accordingly, two or more short connection parts are preferably arranged at intervals along the length of the handle bases.

Preferably, the fiber material uses glass fiber, and the combination ratio of the glass fiber to the synthetic resin material is set at 12 weight % or more and 35 weight % or less. Specifically, if the combination ratio of the glass fiber as the fiber material is less than 12 weight %, the cleaning part is prone to be bent and hard to insert into between adjacent teeth of pore structure. If the combination ratio exceeds 35 weight %, the cleaning part is prone to be broken and may injure inside the mouth of the user, or broken pieces may be accidentally swallowed by the user. Accordingly, the preferred combination ratio is set at 12 weight % or more and 35 weight % or less.

In a preferred embodiment, the synthetic resin material is polypropylene (PP), polybutylene terephthalate (PBT), or polyamide. Preferably in particular, polypropylene is low in molding temperature and can shorten a cycle time of the base part and improve productivity, and imposes less heat load on molding equipment. If polypropylene (PP) is used as the synthetic resin material, the combination ratio of the fiber material is preferably set at 15 weight % or more and 35 weight % or less. If polybutylene terephthalate (PBT) is used, the combination ratio is preferably set at 12 weight % or more and 35 weight % or less.

In a preferred embodiment, the core base is tapered to be gradually reduced in diameter at the leading end thereof, and an angle formed by the tapered shape with respect to the length of the core base is set at 0.2 to 2.5°, and in a further preferred embodiment, 0.2 to 1.5°. According to this embodiment, it is possible to make the cleaning part easier to insert into between teeth, and produce an additional advantage that, on interdental cleaning, the user can use one interdental cleaning tool to gently massage interdental papillae in embrasures of different sizes.

In a preferred embodiment, the elastomer material is a styrene-based elastomer material that has a high flowability even at a low degree of hardness and a favorable adhesion to synthetic resin, as compared to other elastomers, for example, olefin-based elastomers. More specifically; the elastomer material has a Shore A value of 5 to 70, preferably 10 to 50, more preferably 20 to 50, and most preferably 30 to 40.

Advantageous Effects of Invention

According to the method for manufacturing an interdental cleaning tool in the present invention, the synthetic resin material with the fiber material is supplied at a time to the plurality of first molding spaces via the gates at the base ends side of the first molding spaces. Accordingly, the fiber material is oriented along the length of the first molding spaces, that is, the length of the base parts. This makes it possible to improve in particular the core bases in bending strength and buckling strength along the axial direction, and effectively prevent folding and buckling of the core bases at use of the interdental cleaning tools. The fiber material also improves the base parts in dimension stability and strength rigidity to prevent deformation of the core bases. This makes it possible to prevent that at least portions of the core bases in the base parts are defectively charged into the second molding spaces. The fiber material also raises the heat distortion temperature of the core bases, and thus it is possible to effectively prevent softening and deformation of the core bases due to heat generated from the elastomer material at molding of the cleaning flexible parts. The fiber material also raises the strength rigidity of the core bases, and thus it is possible to prevent deformation of the core bases under an injection pressure of the elastomer material. Accordingly, it is possible to prevent the core bases from being deformed at molding of the cleaning flexible parts, and thus it is possible to prevent the molding failure of the cleaning flexible parts in a further effective manner.

The addition of the fiber material allows the plurality of base parts to be connected by the connection parts at an appropriate strength. In addition, even if the manufactured interdental cleaning tools are packaged in a state of being connected by the connection parts, it is possible to prevent that the interdental cleaning tools connected by the connection parts are separated from each other due to vibrations generated in the processes of packaging or distribution/sale. Further, for use, the interdental cleaning tools can be separated on the connection parts by hand in a relatively easy manner. In addition, the fiber material added to the synthetic resin material is also oriented along the length of the first molding spaces, that is, the length of the interdental cleaning tools, around boundary sections between the handle base molding sections and the connection part molding sections. Accordingly, the interdental cleaning tools molded in parallel can be properly cut and separated by bending double the adjacent interdental cleaning tools on the connection parts.

The elastomer material is charged from the leading end sides to the base end sides of the core bases to mold the cleaning flexible parts. This makes it possible to mold the plurality of interdental cleaning tools at a time without complicating the structure of the metal mold for molding the flexible parts. In addition, the core bases are held at two or more longitudinal portions including the leading ends and base ends of the core bases, by at least two pairs of hold pins each of which includes two hold pins opposed to each other in the vertical direction, for example. When opposed hold pins are to be provided in addition to the foregoing two pairs, the same numbers of hold pins are desirably provided on the both opposed surfaces, but different numbers of hold pins may be provided on the both surfaces. The two opposed pins are protruded within the cleaning flexible part molding sections so as to be approximately orthogonal to matching surfaces of the metal mold for molding the flexible parts, that is, protruded in a direction of opening and closing of the metal mold for molding the flexible parts. Accordingly, as compared to conventional cases in which the core bases are held by three or more hold pins at the same positions in a circumferential section along the length of the core bases, it is possible to simplify the structure of the metal mold for molding the flexible parts, and reduce flow resistance of the elastomer material in the cleaning tool molding spaces. It is also possible to suppress influence of Karman vortex generated near the hold pins at charging of the elastomer. In addition, the elastomer material is charged from the leading end sides of the core bases in which the elastomer material is most difficult to flow, which makes it possible to provide sufficient moldability of the leading ends of the cleaning flexible parts.

According to the interdental cleaning tools in the present invention, in the interdental cleaning tools, the fiber material is oriented along the length of the base parts. This makes it possible to improve the core base parts in bending strength and buckling strength along the axial direction, and effectively prevent folding and buckling of the core bases at use of the interdental cleaning tools. The fiber material also improves the base parts in dimension stability and strength rigidity, thereby to prevent deformation of the base parts and mold the cleaning flexible parts with accuracy with respect to the base parts. This makes it possible to realize highquality interdental cleaning tools with accuracy. Further, connecting a plurality of interdental cleaning tools in parallel improves the interdental cleaning tools in moldability and ease of packaging. In addition, at least around the first boundary part of the two boundary parts between the connection part and the handle base, the fiber material is oriented along the length of the handle base. This allows the connection parts to be broken off without deformation of surrounding parts of the connection parts. Accordingly, the interdental cleaning tools connected in parallel can be properly cut and separated at the first boundary parts.

BRIEF DESCRIPTION OF THE DRAWINGS

FIG. 19(a) is a front view of a matching surface of one metal mold for molding base parts in a metal mold device in another configuration, and FIG. 19(b) is a front view of a matching surface of the other metal mold for molding base parts in a metal mold device in another configuration; and FIG. 20(a) is a front view of a matching surface of one metal mold for molding flexible parts in the metal mold device, and FIG. 20(b) is a front view of a matching surface of the other metal mold for molding flexible parts in the metal mold device.

DESCRIPTION OF EMBODIMENTS

Embodiments of the present invention ill be described below with reference to the drawings.

<Interdental Cleaning Tool>

First, a configuration of an interdental cleaning tool 1 will be described.

Figure 1:
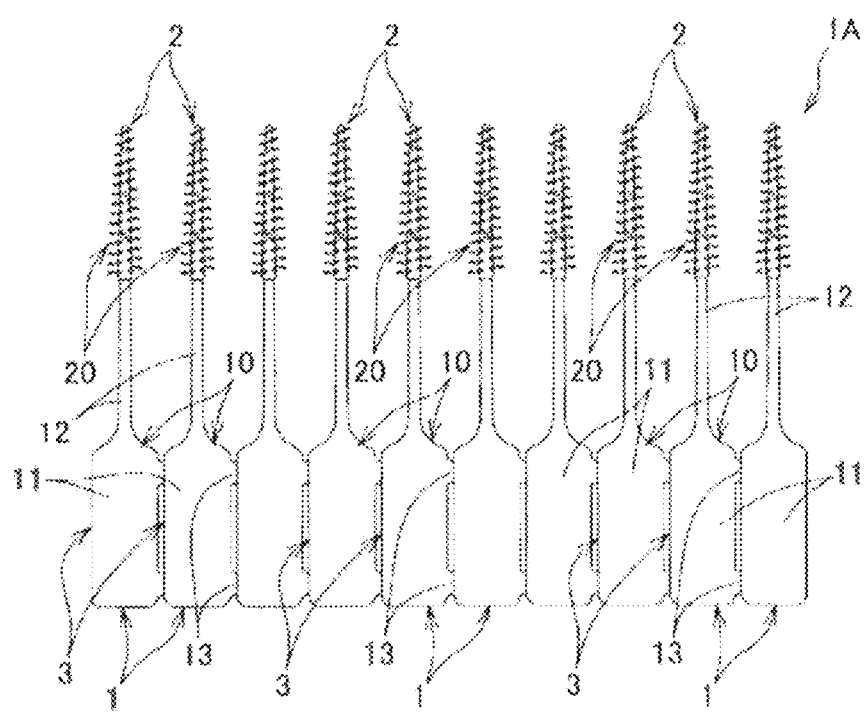
FIG. 1 is a front view of pairs of connected interdental cleaning tools.

As shown in FIGS. 1 to 6, the interdental cleaning tools 1 each include a cleaning part 2 for interdental cleaning and a handle part 3 as a handle in term of functionality, and the interdental cleaning tool 1 includes a base part 10 made of a synthetic resin and a flexible part 20 made of an elastomer in term of material. The interdental cleaning tools 1 are manufactured in the form of an interdental cleaning tool connected body 1A in which a plurality of interdental cleaning tools 1 is connected in parallel so as to be capable of being cut and separated. A user cuts and separates the interdental cleaning tools 1 in sequence on the connection parts 13 from one side of the interdental cleaning tool connected body 1A. FIG. 1 shows the interdental cleaning tool connected body 1A in which ten interdental cleaning tools 1 are connected in parallel, but the number of connected interdental cleaning tools 1 constituting the interdental cleaning tool connected body 1A can be set arbitrarily.

(Base Parts)

The base parts 10 are made of a synthetic resin with a fiber material. As shown in FIGS. 1 to 6, the base parts 10 each includes a flat and elongated plate-like handle base 11 constituting the handle part 3, an elongated shaft-like core base 12 connected to a leading end of the handle base 11, and connection parts 13 connecting the adjacent handle bases 11 so as to be capable of being cut and separated.

The handle base 11 is formed in the shape of a flat and elongated plate. Alternatively, the handle base 11 may be formed in the shape of a bar with a circular, oval, or polygonal cross section, for example, as far as the handle base 11 can be easily held by hand to clean between teeth. The handle base 11 has the leading end that is more narrowed with increasing proximity to the core base 12 and connected smoothly to the core base 12. The dimensions of the handle base 11 can be set arbitrarily as far as the handle base 11 can be easily held by hand to clean between teeth. The handle base 11 in the shape shown in FIGS. 1 to 6 has a length L1 of 10 to 25 mm, a width W1 of 4 to 10 mm, a thickness t1 of a grip portion of 1.0 to 2.0 mm, for example. As in the foregoing, the handle base 11 is made thin, and thus at molding of the base parts 10, it is possible to reduce variations in dimensions due to contraction of the handle bases 11 and prevent occurrence of shrink marks. This prevents charging failure of the base parts 10 into the second metal molds 40 and 41 for molding the flexible parts 20.

The core base 12 is formed in the shape of an almost straight elongated shaft. The core base 12 has on a grip portion side thereof an exposure portion 12a that is exposed to the outside, and has on a leading end side thereof a core main body 12b that is covered with an elastomer and can be inserted into between teeth. The core base 12 is moderately tapered so as to be reduced in diameter at the leading end side. The core base 12 has a length L2 of the exposure portion 12a from an end point of a round (curve) on a side surface of the leading end of the narrow handle base 11 to the base end of the covered portion 20a of the flexible part 20, that is set at, for example, 10 to 50 mm, preferably 10 to 25 mm, in term of operability. The cleaning flexible part 21 has a length L3 that is set at 12 to 22 mm, for example, in term of interdental cleanability. The core base 12 has an angle θ formed by the tapered shape with respect to the center line of the core base 12, that is set at 0.2 to 2.5°, preferably 0.2 to 1.5° in term of ease of insertion into between teeth. The core main body 12b has a diameter of the leading end portion that is set at 0.4 to 0.6 mm, and a diameter of a base end portion that is set at 0.8 to 2.0 mm. The covered portion 21a of the cleaning flexible part 21 has a diameter D of a leading end at the end of a curve that is set at 0.5 to 1.2 min. Accordingly, a leading end portion of the core main body 12b of at least 5 mm or more from the leading end of the core main body 12b can be reliably inserted between teeth. The angle θ formed by the tapered shape of the core base 12 is set to be identical over the entire length of the core base 12. Alternatively, the angle θ may be set to be smaller in a continuous or stepwise manner at the leading end of the core base 12. In addition, the exposure portion 12a may be formed in the shape of a shaft with a diameter identical over the entire length, and only the core main body 12b may be moderately tapered so as to be reduced in diameter at the leading end. Further, the exposure portion 12a may be omitted to connect the core main body 12b direct to the handle base 1.

Figure 2:
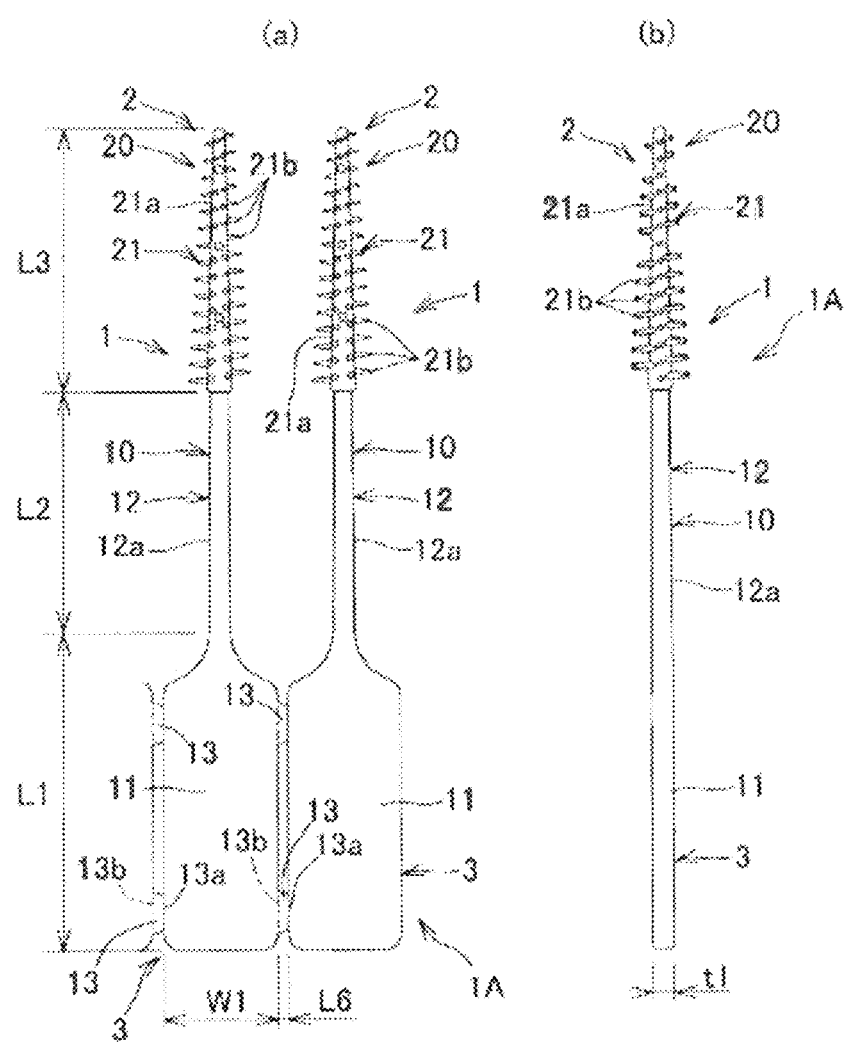
FIG. 2(a) is a front view of interdental cleaning tools.
FIG. 2(b) is a side view of an interdental cleaning tool.
Figure 3:
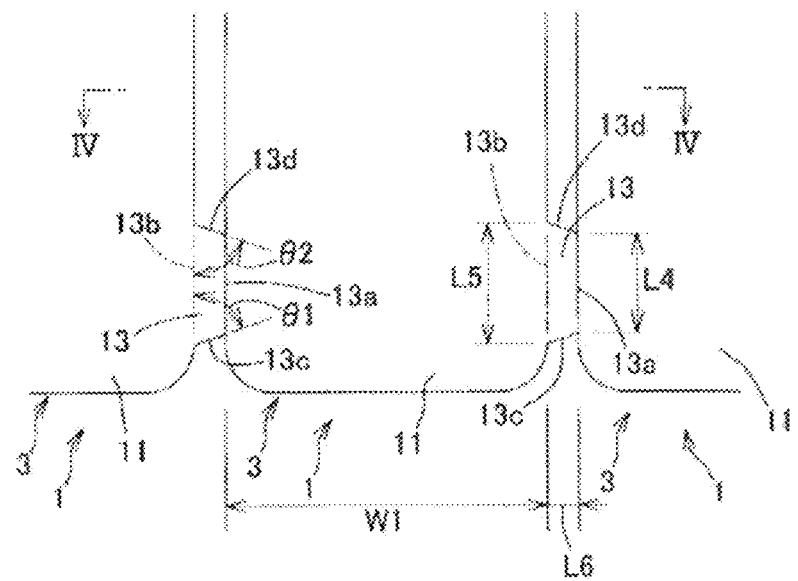
FIG. 3 is an enlarged front view of connection parts and surrounding parts in the interdental cleaning tools.
Figure 4:
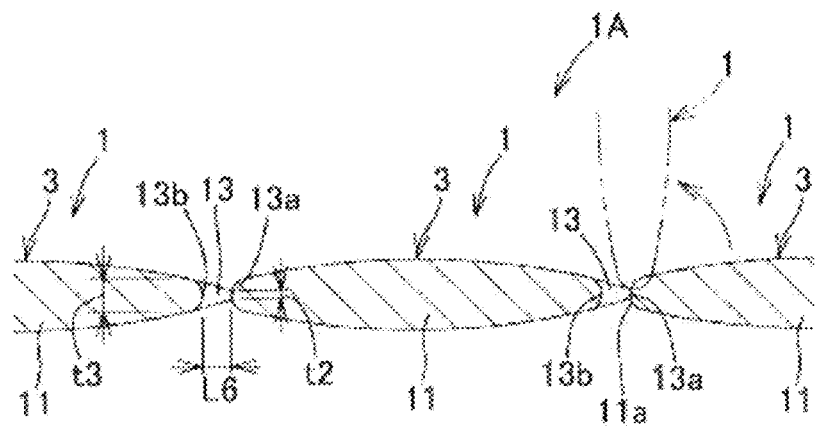
FIG. 4 is a cross section view of FIG. 3 taken along line IV-IV.
Figure 5:
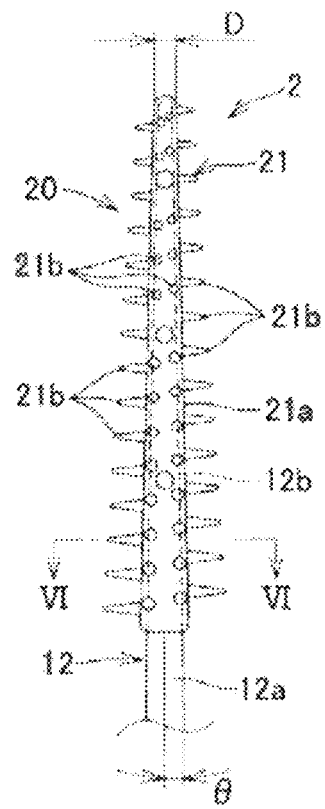
FIG. 5 is an enlarged view of a cleaning part.
Figure 6:
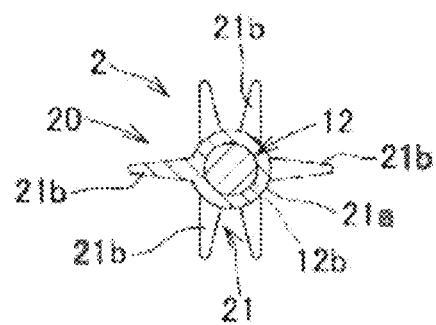
FIG. 6 is a cross section view of FIG. 5 taken along line VI-VI.

As shown in FIGS. 2 to 4, the connection parts 13 are formed between the adjacent handle bases 11 so as to be integrated with the handle bases 11. One each pair of connection parts 13 is provided at intervals along the length of the base end side and the leading end side of the handle base 11. Boundary parts 13a and 13b between the adjacent handle bases 11 and the connection part 13 between the handle bases 11 have lengths L4 and L5 that are set at 1.5 to 3.0 mm, for example. The length L4 of the first boundary part 13a is set smaller than the length L5 of the second boundary part 13b. The connection parts 13 are elongated along the length of the handle bases 11 and are formed in the shape of a trapezoid (isosceles trapezoid in FIG. 3) in a front view. The number of the connection parts 13 can be arbitrarily set, and thus only one connection part can be arranged. In this case, however, it is not possible to provide sufficient connection strength of the adjacent base parts 10 at manufacture of the interdental cleaning tools 1. Thus, after molding of the base parts 10, the connection parts 13 may be broken at opening of the molds to let the base parts 10 fall apart and disable molding of the flexible parts 20, or the connection parts 13 may be folded and bent to interfere with charging of the base parts 10 into proper positions of the second molding spaces 42 for molding the flexible parts 20, thereby resulting in molding failure. Accordingly, two or more connection parts 13 are preferably provided at intervals along the length of the handle bases 11.

The connection part 13 has a protrusion length L6 that is set at 0.5 to 1.5 mm, for example. A thickness t2 of the connection part 13 at the first boundary part 13a is set smaller than a thickness t3 of the connection part 13 at the second boundary part 13b. The connection part 13 is made thinner in a continuous or stepwise manner from the second boundary part 13b to the first boundary part 13a. The connection part 13 has a cross section formed in the shape of a trapezoid or triangle (isosceles trapezoid or isosceles triangle in FIG. 4). As shown by a virtual line in FIG. 4, when the adjacent interdental cleaning tools 1 are bent double on the first boundary part 13a to concentrate a bending force on the first boundary part 13a and bring a circular side surface 11a at a side edge of the handle base 11 is into contact with an outer surface of the connection part 13, a large force for separating the interdental cleaning tools 1 on the principle of leverage acts on the first boundary part 13a. Accordingly; the interdental cleaning tools 1 can be properly cut and separated without large deformation of the connection part 13 at the first boundary part 13a. A thickness t2 of the connection part 13 at the first boundary part 13a is preferably set at 0.10 to 0.25 mm, for example, in particular most preferably 0.15 mm. A thickness t3 of the connection part 13 at the second boundary part 13b is preferably set at 0.60 to 0.80 mm, for example, in particular most preferably 0.65 mm. The connection part 13 can be formed in an arbitrary shape as far as the connection part 13 allows the adjacent interdental cleaning tools 1 to be easily and properly cut and separated by bending double the interdental cleaning tools 1 on the connection part 13. In addition, the connection part 13 may be made thinnest at a middle portion along the protrusion length L6. In this case, however, it is difficult to act a large force on the first boundary part 13a in a direction in which the interdental cleaning tools 1 are separated on the principle of the leverage. Thus, the connection part 13 is preferably made thinnest at one end in a direction of protrusion. In addition, the connection part 13 has an inner angle θ1 of an oblique side 13c at the base end side of the handle base 11 and an inner angle θ2 of an oblique side 13d at the leading end side of the handle base 11. The angles θ1 and θ2 can be set arbitrarily, but are preferably set smaller than 90°. If the inner angles θ1 and θ2 are set at different angles, the inner angle θ1 of the oblique side 13c at the base end side is preferably set smaller than the inner angle θ2 of the oblique side 13d at the leading end side. Accordingly, it is possible to orient the fiber material included in the synthetic resin material along the length of the handle base 11 near the first boundary part 13a, and allow the synthetic resin material supplied to the adjacent handle base 11 to join near the first boundary part 13a. This further improves ease of cutting and separating the interdental cleaning tools 1 at the first boundary part 13a.

The synthetic resin material for the base parts 10 may be any of thermoplastic synthetic resin materials such as polypropylene (PP), polybutylene terephthalate (PBT), polyethylene, polyethylene terephthalate, polycyclohexylene dimethylene terephthalate, saturated polyester resin, polymethylmethacrylate cellulose propionate, polyurethane, polyamide, polycarbonate, ABS (acrylonitrile butadiene styrene), and the like. In particular, polypropylene (PP) and polybutylene terephthalate (PBT) are preferred because these materials prevent breakage of the base parts 10. Most preferred is polypropylene that is low in molding temperature, can shorten a cycle time and improve productivity, and imposes less heat load on molding equipment.

The fiber material added to the synthetic resin material for the base parts 10 may be glass fibers, carbon fibers, aramid fibers, or the like. The combination ratio of the fiber material depends on the synthetic resin material for the base parts 10. Basically, if the combination ratio is less than 12 weight %, the synthetic resin material is prone to be bent and the cleaning part 2 is hard to insert into between teeth, and if the combination ratio exceeds 35 weight %, the cleaning part 2 is prone to be broken. Accordingly, the combination ratio is preferably set at 12 weight % or more and 35 weight % or less, more preferably 15 weight % or more and 35 weight % or less, in particular preferably 20 weight % or more and 30 weight % or less. Specifically, if polypropylene (PP) is used as the synthetic resin material, the combination ratio of the fiber material is preferably set at 15 weight % or more and 35 weight % or less, if polybutylene terephthalate (PBT) is used as the synthetic resin material, the combination ratio of the fiber material is preferably set at 12 weight % or more and 35 weight % or less, and 15 weight % or more and 35 weight % or less.

The fiber material is preferably oriented along the length of the base part 10. According to this configuration, it is possible to improve the base part 10 in bending strength and buckling strength along the axial direction, thereby to effectively prevent the core bases 12 from being broken and buckled at use of the interdental cleaning tool 1. In addition, when the fiber material is oriented along the length of the base part 10, the fiber material is also oriented along the length of the base part 10 even at the first boundary part 13a of the connection part 13. Accordingly, the interdental cleaning tools 1 molded in parallel can be properly cut and separated at the first boundary parts 13a by bending double the adjacent interdental cleaning tools 1 on the first boundary portion 13a. The addition of the fiber material also improves the base parts 10 in dimension stability and strength rigidity to prevent deformation of the base parts 10. This makes it possible to prevent that the base parts 10 are defectively charged into the second molding spaces 42 of the second metal molds 40 and 41. The fiber material also raises the heat distortion temperature of the core bases 12, and thus it is possible to effectively prevent softening and deformation of the core bases 12 due to heat generated from the elastomer material at molding of the cleaning flexible parts 21. The fiber material also raises the strength rigidity of the core bases 12, and thus it is possible to prevent deformation of the core bases 12 under a pressure of injection of the elastomer material. Accordingly, it is possible to effectively prevent the molding failure of the cleaning flexible parts 21.

(Flexible Part)

The flexible part 20 is molded using the elastomer material so as to be integrated with the base part 10, and includes a cleaning flexible part 21 put on the core base 12, as shown in FIGS. 1 to 6. As the flexible part 20, an annular insert regulation part can be provided at the base end of the core main body 12b to regulate insertion into between teeth, or an anti-slip part can be provided at the handle base 11. The insert regulation part or the anti-slip part can be molded independently from the cleaning flexible part 21, but in this case, the metal mold structure is complicated. Accordingly; the insert regulation part or the anti-slip part is preferably molded so as to be connected to the base of the cleaning flexible portion 21.

The cleaning flexible part 21 has a covered portion 21a covered by the core base 12 and a plurality of protrusions 21b that is formed at intervals so as to protrude outward at intervals along the length of the covered portion 21a.

If a wall thickness of the covered portion 21a is too large, it is necessary to reduce the diameter of the core main body 12b covered by the covered portion 21a. This causes undesirably the cleaning part to be significantly lowered in rigidity when being inserted into between teeth, and raises the possibility that Karman vortex is prone to be generated in the molding process and the cleaning part is subject to great influence of the Karman vortex. If the wall thickness of the covered portion 21a is too small, the elastomer material cannot be charged into the base end of the cleaning part 2, undesirably. Accordingly the wall thickness of the covered portion 21a is preferably set at 0.1 to 0.2 mm.

The protrusions 21b are formed at intervals therebetween along the length of the covered portion 21a and positioned at intervals therebetween along a circumferential direction of the covered portion 21a. More specifically, to allow the protrusions 21b to be molded by second metal molds 40 and 41 described below, six kinds of protrusions 21b are arranged at the covered portion 21a in the circumferential direction: a set of two protrusions 21b protruding from the covered portion 21a toward one side of a direction of opening/closing of the metal molds; a set of two protrusions 21b protruding from the covered portion 21a toward the other side of the direction of opening/closing of the metal molds; one protrusion 21b protruding from the covered portion 21a toward the one side along matching surfaces 40a and 41a; and one protrusion 21b protruding from the covered portion 21a toward the other side along the matching surfaces 40a and 41a. A plurality of sets of the six kinds of protrusions 21b is formed at intervals therebetween along the length of the covered portion 21a. Alternatively, the protrusions 21b may be formed in arrangement patterns other than the foregoing one.

The cross section area of base ends of the protrusions 21b, the length of the protrusions 21b, and the number and arrangement pitch of the protrusions 21b can be set arbitrarily. In term of moldability and cleanability, the cross section area of the base ends of the protrusions 21b is preferably set at about 0.03 to 1.5 mm$^2$. The length of the protrusions 21b is preferably set at about 0.5 to 2.0 mm. The number of the protrusions 21b is preferably set at 20 to 100. The arrangement pitch of the protrusions 21b is preferably set at 0.5 to 1.5 mm. In addition, the protrusions 21b herein are formed in the shape of a circular cone, but the protrusions 21b may be formed in the shape of a tapered plain plate that is made flat along the axial direction. Further, the cross section of the protrusion 21b may not only be formed in the shape of a circle but may also be formed in an arbitrary shape such as an oval, a polygon, or the like.

The elastomer for the flexible parts 20 may be any of thermoplastic elastomers such as styrene-based, olefin-based, and polyamide-based elastomers, nylon-based elastomers of 6 nylon, 6-6 nylon, 6-10 nylon, and 6-12 nylon, and thermosetting elastomers such as silicon rubber, urethane rubber, fluoro-rubber, natural rubber, and synthetic rubber. In particular, the elastomer material is preferably compatible with the synthetic resin material for the base parts 10. For example, if the base parts 10 are to be made of polypropylene, the flexible parts 20 are preferably made of a poly-olefin-based elastomer or a styrene-based elastomer.

<Manufacturing Method>

Next, a method for manufacturing the interdental cleaning tool 1 will be described.

As shown in FIGS. 7 to 12, the method for manufacturing the interdental cleaning tool 1 includes: a base part molding step of charging a synthetic resin material into first molding spaces 32 of first metal molds 30 and 31 to produce the base parts 10; and a flexible part molding step of setting the base parts 10 molded by the first metal molds 30 and 31 into second molding spaces 42 of second metal molds 40 and 41, and then charging an elastomer material into the second molding spaces 42 to mold the flexible parts 20.

(Base Part Molding Step)

Figure 7:
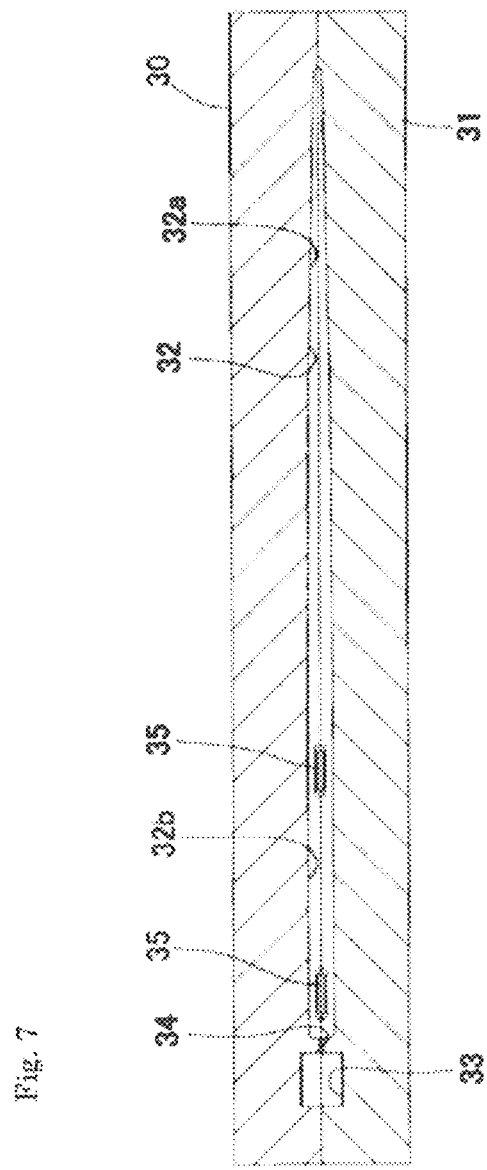
FIG. 7 is a diagram describing a method for molding a base part by a first metal mold.
Figure 8:
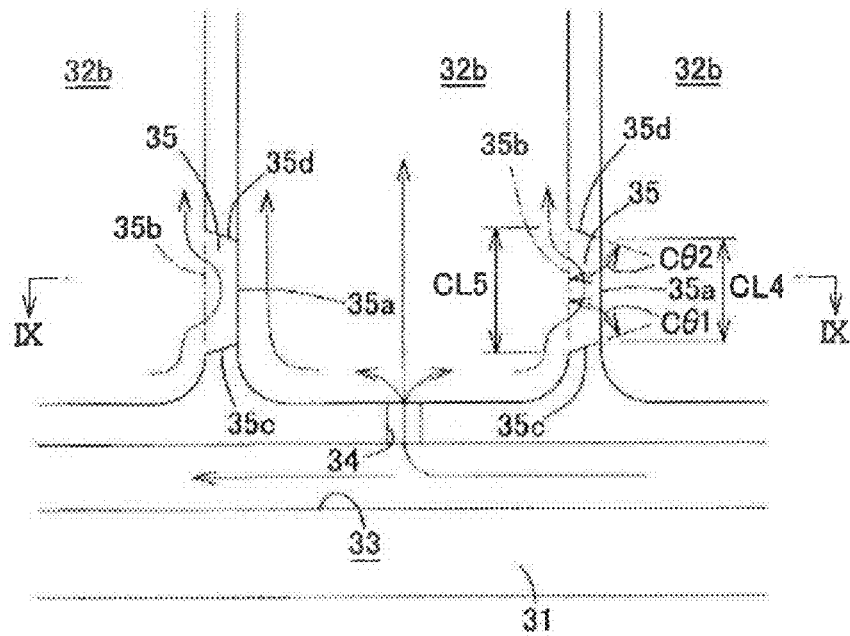
FIG. 8 is a front view of a matching surface of the first metal mold near connection part molding sections.
Figure 9:
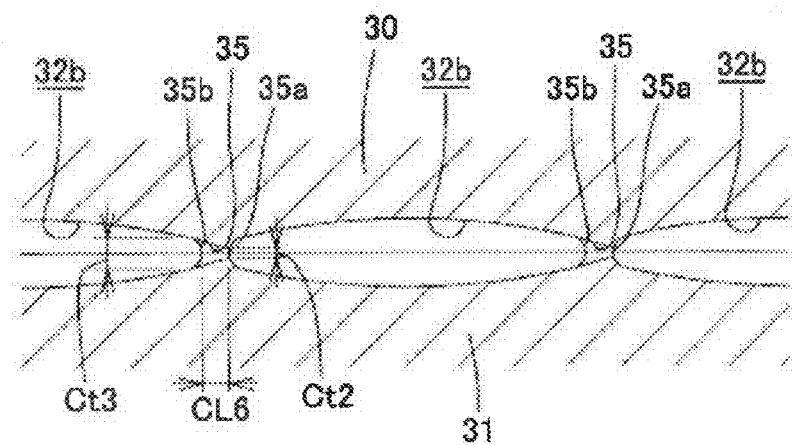
FIG. 9 is a cross section view of the first metal mold shown in FIG. 8 taken along line IX-IX.

At the base part molding step, as shown in FIGS. 7 to 9, a synthetic resin material with a fiber material is charged into the first molding spaces 32 of the first metal molds 30 and 31 to produce the base parts 10. More specifically, the plurality of base parts 10 is produced at a time in such a manner as to: arrange in parallel, as the first metal molds 30 and 31, a plurality of first molding spaces 32 including core base molding sections 32a and handle base molding sections 32b; form pairs of connection part molding sections 35 between the adjacent handle base molding sections 32b so as to communicate with the adjacent handle base molding sections 32b; form runners 33 at base end sides of the first molding spaces 32; communicate the runners 33 via gates 34 with the first molding spaces 32; and supply a synthetic resin material with a fiber material to the runners 33 to charge the synthetic resin material with the fiber material via the gates 34 into the first molding spaces 32. Accordingly; a primary molded article 10A including the plurality of base parts 10, the runner parts 37, the gate parts 36, and the connection parts 13, is produced. The base parts 10 can be molded one by one. However, the base parts 10 are preferably molded at a time with improved productivity and workability because, in this case, it is possible to transfer the base parts 10 at a time while holding molded runner parts 37. The gates 34 may be formed at arbitrary positions at the base end sides of the first molding spaces 32 opposite to the core base molding sections 32*a*, more preferably, nearer an edge than the connection part molding sections 35 at the base end side of the first molding spaces 32 opposite to the core base molding sections 32*a*. Preferably, side gates as the gates 34 are formed at the base ends of the first molding spaces 32 to reduce a risk that, when the primary molded article 10A is charged into the second metal molds 40 and 41, gates 36 of the primary molded article 10A get caught between the second metal molds 40 and 41. Instead of the runners 33 as cold runners, hot runners may be provided at the first metal molds 30 and 31, but the use of the hot runners leads to the larger-sized first metal molds 30 and 31 and higher manufacturing costs. Accordingly, it is preferred to provide the runners 33 as cold runners. The runner parts 37 make it possible to connect a plurality of base parts 10 in a stable manner, whereby the primary molded article 10A can be transferred to the second metal molds 40 and 41 with improved handling property. As the gates 34, cylindrical or spindle-shaped pin gates with a diameter of 0.1 to 1.5 mm, for example, can be preferably employed to allow use of cold runners and reduction of intervals between the gates 34, thereby to produce a molded article in a smaller size.

As shown in FIGS. 7 to 9, the connection part molding sections 35 are formed in the same size as that of the connection parts 13 molded thereby. Lengths CL4 and CL5 of boundary sections 35*a* and 35*b* between the adjacent handle base molding sections 32*b* and the connection part molding sections 35 between the two handle base molding sections 32*b* are set at 1.5 to 3.0 mm, for example. The length CL4 of the first boundary sections 35*a* is set shorter than the length CL5 of the second boundary sections 35*b*. The connection part molding sections 35 are elongated along the length of the handle base molding section 32*b*, and are formed in the shape of a trapezoid in a front view (isosceles trapezoid in FIG. 8).

Length CL6 of the connection part molding sections 35 is set at 0.5 to 1.5 mm, for example. Thickness Ct2 of the connection part molding sections 35 at the first boundary sections 35*a* is set smaller than thickness Ct3 of the connection part molding sections 35 at the second boundary sections 35*b*. The connection part molding sections 35 are configured to be thinner in a continuous or stepwise manner from the second boundary sections 35*b* to the first boundary sections 35*a*. The cross sections of the connection part molding sections are formed in the shape of a trapezoid or a triangle (isosceles trapezoid or isosceles triangle in FIG. 9).

The thickness Ct2 of the connection part molding sections 35 at the first boundary sections 35*a* is preferably set at 0.10 to 0.25 mm, for example, optimally at 0.15 mm. The thickness Ct3 of the connection part molding sections 35 at the second boundary sections 35*b* is preferably set at 0.60 to 0.80 mm, for example, optimally at 0.65 mm.

The number of the connection part molding sections 35 can be arbitrary set. The connection part molding section 35 may be only one. In this case, however, it is not possible to provide sufficient connection strength of the adjacent base parts 10, and thus after molding of the base parts 10, the connection parts 13 may be broken to let the base parts 10 fall apart at the time of mold opening, or the connection parts 13 may be folded to interfere with charging of the base parts 10 into proper positions of the second molding spaces 42, thereby resulting in molding failure. Accordingly, two or more connection part molding sections 35 are preferably provided at intervals along the length of the handle base molding sections 32*b*.

At the base part molding step, a synthetic resin material with a fiber material is supplied at a time to the plurality of first molding spaces 32 via the gates 34 at the base ends of the first molding spaces 32 nearer edges than the connection part molding sections 35. Accordingly, the fiber material is oriented along the length of the first molding spaces 32, that is, the length of the base parts 10. This makes it possible to improve the base parts 10 in bending strength and buckling strength along the axial direction, and prevent effectively folding and buckling of the core bases 12 at use of the interdental cleaning tools 1. The fiber material also improves the base parts 10 in dimension stability and strength rigidity to prevent deformation of the base parts 10. This makes it possible to prevent that the base parts 10 are defectively charged into the second molding spaces 42 of the second metal molds 40 and 41. The fiber material also raises the heat distortion temperature of the core bases 12, and thus it is possible to prevent effectively softening and deformation of the core bases 12 due to heat from the elastomer material generated at molding of the cleaning flexible parts 21. The fiber material also raises the strength rigidity of the core bases 12, and thus it is possible to prevent deformation of the core bases 12 under a pressure of injection of the elastomer material. Accordingly, it is possible to prevent the core bases 12 from being deformed at molding of the cleaning flexible parts 21, and thus it is possible to prevent the molding failure of the cleaning flexible parts 21 in a further effective manner.

Figure 13:
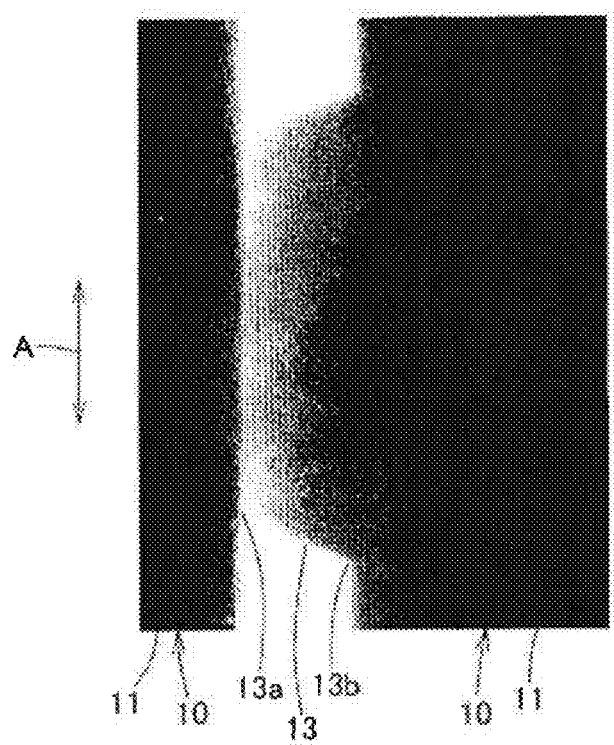
FIG. 13 is a photograph showing orientation of a fiber material at the connection part and the surrounding part.

As shown by arrows in FIG. 8, the synthetic resin material flows from the gates 34 to the handle base molding sections 32*b*. The length CL4 of the connection part molding sections 35 at the second boundary sections 35*b* is set longer than the length CL1 of the connection part molding sections 35 at the first boundary sections 35*a*, and the thickness Ct3 of the connection part molding sections 35 at the second boundary sections 35*b* is set larger than the thickness Ct2 of the connection part molding sections 35 at the first boundary sections 35*a*. Thus, even if the synthetic resin material reaches simultaneously the both boundary sections 35*a* and 35*b*, the synthetic resin material is charged from the second boundary section 35*b* side into the connection part molding sections 35, and thus the synthetic resin material flowing into the adjacent first molding spaces 32 join together near the first boundary sections 35*a*. Accordingly, the synthetic resin material supplied to the adjacent handle base molding sections 32*b* join near the first boundary sections 35*a*, and thus the molded base parts 10 can be easily cut and separated at positions corresponding to the first boundary sections 35*a*. In addition, the synthetic resin material flows into the connection part molding sections 35 as shown by arrows in FIG. 8, and thus the fiber material added to the synthetic resin material is prone to be oriented along the length of the handle base molding sections 32*b* at the first boundary sections 35*a* of the connection part molding sections 35 as shown in FIG. 13. This also allows the base parts 10 to be easily cut and separated at positions corresponding to the first boundary sections 35*a*. Accordingly, the interdental cleaning tools 1 can be properly cut and separated in sequence at the first boundary sections 13*a* from one side of the molded interdental cleaning tool connected body 1A by bending double the adjacent interdental cleaning tools 1 on the first boundary part 13*a* therebetween. However, it is necessary to set the connection strength between the connection parts 13 and the base parts 10 such that the base parts 10 connected in parallel are not separated from each other when transferred from the first metal molds 30 and 31 to the second metal molds 40 and 41.

Figure 10:
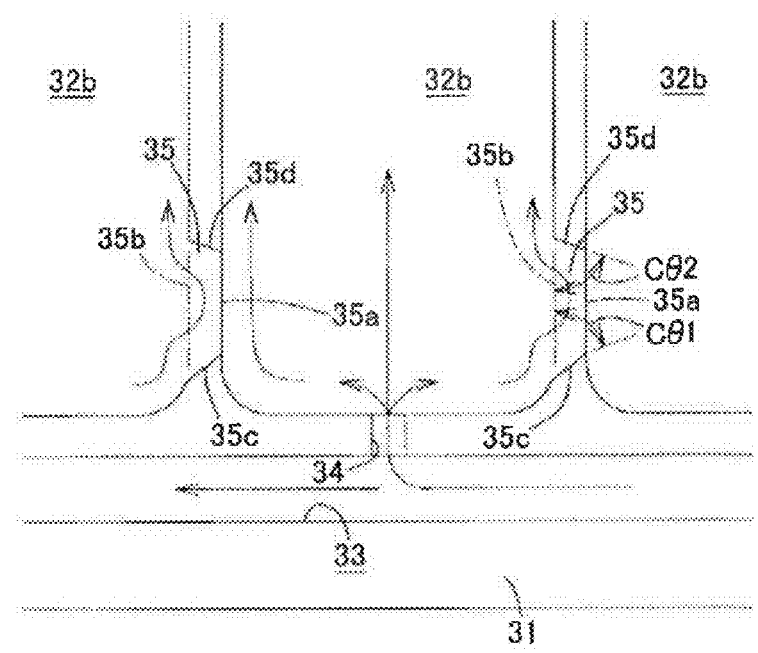
FIG. 10 is a front view of a matching surface of a first metal mold near connection part molding sections in another configuration.

In the connection part molding section 35, an inner angle Cθ1 of an oblique side 35c of the handle base molding section 32b at the base end side and an inner angle Cθ2 of an oblique side 35d of the handle base molding section 32b at the leading end side, can be set at arbitrary values. Preferably, these angles are set smaller than 90°. If the inner angles Cθ1 and Cθ2 are tube set at different values, it is preferred as shown in FIG. 10 to set the inner angle Cθ1 of the oblique side 35c at the base end side smaller than the inner angle Cθ2 of the oblique side 35d at the leading end side. Accordingly; it is possible to facilitate flowing of the synthetic resin material from the base sides of the second boundary sections 35b into the connection part molding sections 35, and allow the fiber material near the first boundary sections 35a to be oriented further properly along the length of the handle base molding sections 32b. In addition, the synthetic resin material is further prone to join near the first boundary sections 35a, and thus the interdental cleaning tools 1 can be further easily cut and separated at the first boundary sections 35a.

(Flexible Part Molding Step)

Figure 11:
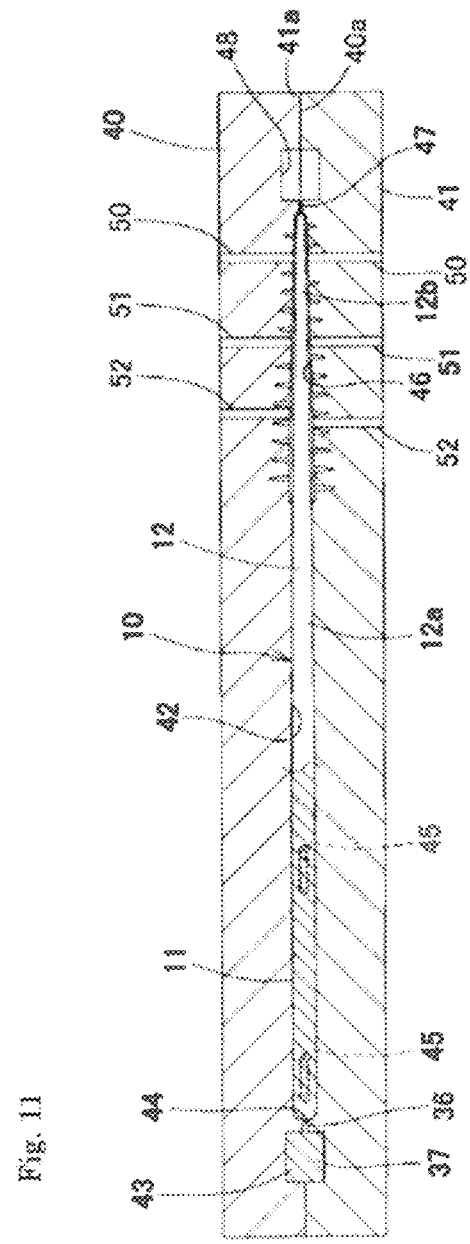
FIG. 11 is a diagram describing a method for molding a flexible part by a second metal mold.
Figure 12:
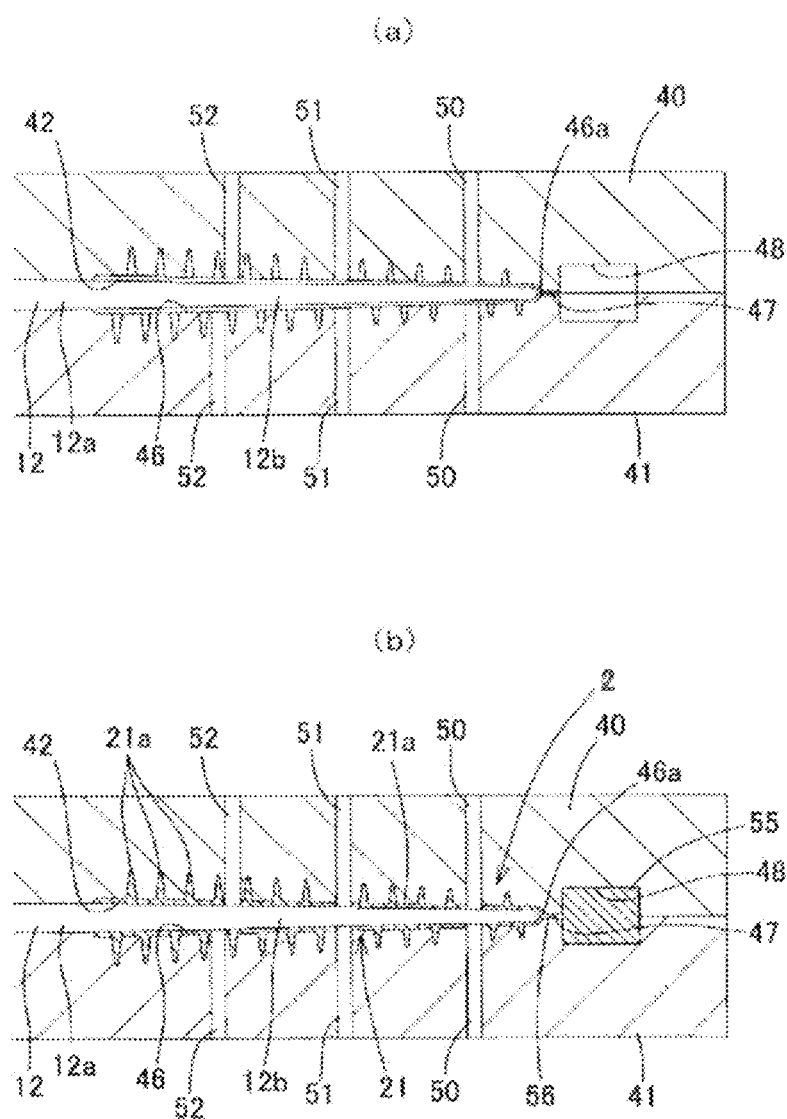
FIG. 12(a) is an enlarged view of a cleaning flexible part molding section and a surrounding section in the second metal mold before protrusion of hold pins.
FIG. 12(b) is an enlarged view of the cleaning flexible part molding section and the surrounding section in the second metal mold after protrusion of the hold pins.

At the flexible part forming step, as shown in FIGS. 11 and 12, the primary molded article 10A molded at the first metal molds 30 and 31 are set into the second molding spaces 42 of the second metal molds 40 and 41, and then an elastomer material is charged into the second molding spaces 42 to mold the flexible parts 20, thereby obtaining the interdental cleaning tool connected body 1A in which the plurality of interdental cleaning tools 1 is connected in parallel.

First, the second metal molds 40 and 41 used at the flexible part molding step will be described, below. The second metal molds 40 and 41 are provided with the plurality of second molding spaces 42 at positions corresponding to the plurality of base parts 10 in the primary molded components 10A molded at the first metal molds 30 and 31. The second metal molds 40 and 41 are also provided with fitting spaces 43, 44, and 45 adapted to the runner parts 37, the plurality of gate parts 36, and the connection parts 13 of the primary molded article 10A. Formed between the second metal molds 40 and 41 and the base parts 10 are cleaning flexible part molding sections 46 surrounding the core bases 12, as second molding spaces 42. At leading end sides of the cleaning flexible part molding sections 46, gates 47 are formed on matching surfaces 40a and 41a of the second metal molds 40 and 41 and are opened at the leading ends of the cleaning flexible part molding sections 46. The gates 47 communicate with common runners 48 formed in the second metal molds 40 and 41 such that the elastomer material is supplied from the common runners 48 through the gates 47 to the second molding spaces 42. The diameter of the gates 47 is preferably set to be equal to or larger than 0.1 mm or equal to or smaller than 1.0 mm.

The second metal molds 40 and 41 are provided with a pair of leading end-side hold pins 50, a pair of middle portion hold pins 51 (the middle portion hold pins 51 may be provided as appropriate or may be omitted), and a pair of base end-side hold pins 52, corresponding to the leading end-side portion, middle portion, and base end-side portion of the cleaning flexible part molding section 46, respectively. The three pairs of hold pins 50 to 52 are capable of movement in a direction approximately orthogonal to the matching surfaces 40a and 41a of the second metal molds 40 and 41, in other words, in a direction of opening and closing of the second metal molds 40 and 41. As shown in FIG. 12 (b), the core bases 12 of the base parts 10 are positioned and held with high accuracy at centers of the cleaning flexible part molding sections 46 by protruding leading ends of the three pairs of hold pins 50 to 52 into the cleaning flexible part molding sections 46, and sandwiching the core bases 12 between the leading ends of the hold pins 50 to 52.

Of the hold pins 50 to 52, the leading end-side hold pins 50 have the smallest cross section area, and the middle portion hold pins 51 and the base end-side hold pins 52 have larger cross section areas in the order of the middle portion hold pins 51 then the base end-side hold pins 52 or in the order of the base end-side hold pins 52 then the middle portion hold pins 51. That is, the cleaning flexible part molding sections 46 have a smaller path area at the leading end-side portions. Accordingly, when the cross section area of the leading end-side hold pins 50 is made the smallest, it is possible to decrease flow resistance of the elastomer material as much as possible, and suppress influence of Karman vortex generated in the molding process. This preferably prevents a failure of charging of the elastomer material into the cleaning flexible part molding sections 46, and prevents excessive melting of the core base 12. Alternatively, the hold pins 50 to 52 may be set to be equal in cross section area. In addition, a plurality of pairs of the middle portion hold pins 51 can be provided at intervals along the axial direction, or the middle portion hold pins 51 may be omitted. In this embodiment, the cross sections of the hold pins 50 to 52 are formed in a circle. Alternatively, to further suppress influence of Karman vortex in the molding process, the cross sections of the hold pins 50 to 52 may be formed in an oval elongated along the length of the cleaning flexible part molding sections 46, a long circle, or an asymmetric shape with respect to a central axis (for example, teardrop shape), or the like.

The leading end-side hold pins 50 are provided at positions where leading ends of the pins are in contact with the core base corresponding to a range of 3 mm from the leading end portion 46a toward the base end side of the cleaning flexible part molding section 46. The leading ends and surrounding portions of the leading ends of the leading end-side hold pins 50 have a cross section area of 0.03 to 0.3 mm$^2$. The middle portion hold pins 51 are provided at positions where the leading ends of the pins are in contact with the core base corresponding to a range of ±10% of length of the cleaning part 2 along the axial direction with a center at a middle point between the leading end-side hold pins 50 and the base end-side hold pins 52, and the leading ends and surrounding portions of the leading ends of the middle portion hold pins 51 have a cross section area of 0.12 to 1.2 mm$^2$. The base end-side hold pins 52 are provided at positions where the leading ends of the pins are in contact with the core base corresponding to a range of 6 mm from the base end portion toward the leading end side of the cleaning flexible part molding section 46, and the leading ends and surrounding portions of the leading ends of the base end-side hold pins 52 have a cross section area of 0.1 to 1.1 mm$^2$. Because of the foregoing settings, the core bases 12 can be reliably fixed in the molding process, and it can be expected that influence of Karman vortex generated in the molding process is prevented from exerting on the molded body.

The hold pins 50 to 52 may have leading end surfaces abutting the core bases 12 that are flat and orthogonal to the axial direction of the hold pins 50 to 52. Preferably, the leading end surfaces are formed as circular surfaces along outer peripheral surfaces of the core bases 12, thereby to improve the property of holding the core bases 12.

The pair of leading end-side held pins 50 and the pair of middle portion hold pins 51 are each coaxially arranged. Meanwhile, the pair of base end-side hold pins 52 is arranged such that an axial line thereof is displaced by a length of 0.1 to 1.0 times the diameter of the base end-side hold pins 52, for example, along the length of the cleaning flexible part molding sections 46. If the pair of hold pins 52 is displaced along the length of the cleaning flexible part molding sections 46, when the core bases 12 are held between the hold pins 52, the hold pins 52 are pressed and attached by a substantially wider area to the core bases 12. Accordingly, the hold pins 52 can hold the core bases 12 more firmly. The hold pins to be displaced along the length of the cleaning flexible part molding sections 46 may be one or two or more selected from the hold pins 50 to 52. The foregoing settings make it possible to fix the core bases 12 more firmly in the molding process. In addition, it can be expected that the influence of Karman vertex generated in the molding process is prevented from exerting on the molded body.

At the flexible part molding step, when the primary molded article 10A is set into the second molding spaces 42 and the metal molds are closed as shown in FIG. 12 (a), the pair of leading end-side hold pins 50, the pair of middle portion hold pins 51, and the pair of base end-side hold pins 52 are protruded into the cleaning flexible part molding sections 46, thereby to hold the core bases 12 by the three pairs of hold pins 50 to 52. Then, the elastomer material is injected and supplied to the gates 47 through the runners 48 to charge the elastomer material into the cleaning flexible part molding sections 46. Since the cross section areas of the hold pins 50 to 52 are larger with increasing proximity to the base portions of the cleaning flexible part molding sections 46, it is possible to hold the core bases 12 in a stable manner by increasing contact areas of the hold pins 50 to 52 and the core bases 12, while preventing as much as possible that the hold pins 50 to 52 interfere with charging of the elastomer material from the leading end portions to the base end side of the cleaning flexible part molding sections 46. Accordingly, even with certain variations in injection pressure, it is possible to mold the cleaning flexible parts 21 from the elastomer material with high accuracy, while preventing curvature of the core bases 12.

Then, the base parts 10 are covered with the flexible parts 20, the runner parts 37 and the gate parts 36 made of the synthetic resin are removed from the base parts 10 and the flexible parts 20, and the runner parts 55 and the gate parts 56 of the elastomer molded at the runners 48 and the gates 47 are removed, from the base parts 10 and the flexible parts 20, thereby obtaining the interdental defining tools 1.

Next, an evaluation test on the interdental cleaning tools 1 will be described.

Six kinds of interdental cleaning tools 1 were manufactured in such a manner that synthetic resin materials were prepared by adding glass fibers as a fiber material to polypropylene (PP) at combination ratios of 0 weight %, 10 weight %, 20 weight %, 30 weight %, 40 weight %, and 50 weight %; these synthetic resin materials were used to six kinds of base parts 10; and cleaning flexible parts 21 made of a polystyrene-based elastomer were molded on core bases 12 of the six kinds of base parts 10.

The first metal molds 30 and 31 were provided with the first molding space 32 sized such that the core base body 12b of the base part 10 molded by the first metal molds 30 and 31 have a length of 15 mm, an angle θ of 2.0° formed by the tapered shape along the length, a diameter of 0.45 mm at a leading end side, and a diameter of 1.0 mm at abuse. The second metal molds 40 and 41 are configured such that: there is a gap of 0.15 mm between an inner surface of a cleaning flexible part molding section 46 and the outer surface of the core main body 12b; a leading end-side hold pin 50 with a cross section area of 0.2 mm$^2$ is provided at a position of 2 mm from the leading end to the base end side of the cleaning flexible part molding section 46; an middle portion hold pin 51 with a cross section area of 0.4 mm$^2$ is provided at a position of 6 mm from the leading end to the base end side of the cleaning flexible part molding section 46; and a base end-side hold pin 52 with a cross section area of 0.3 mm$^2$ is provided at a position of 10 mm from the leading end to the base end side of the cleaning flexible part molding section 46.

Then, the six kinds of interdental cleaning tools 1 were set in sequence in portrait orientation in an autograph (manufactured by Shimadzu Corporation), and were subjected to a compression test at a compression rate 10 mm/min. Table 1 shows results of the compression test.

The six kinds of interdental cleaning tools 1 were subjected to a sensory test by ten examiners for the presence or absence of bending of the cleaning parts 2 in use, and for insertability of the cleaning parts 2 into between teeth. Table 1 shows results of the sensory test.

To check the base parts 10 for dimension stability with addition of an additive, the six kinds of base parts 10 were measured in heat distortion temperature and molding shrinkage ratio in a flow direction of the synthetic resin material and a direction orthogonal to the flow direction in the first molding spaces 32. In addition, a hundred base parts 10 each of the six kinds were molded. Of the hundred base parts 10, the number of defective base parts 10 incapable of being fitted into the second molding spaces 42 of the second metal molds 40 and 41, was counted. Table 1 shows results of the measurements and counts.

TABLE 1

| Combination amount of glass fibers (weight %) | | 0% | 10% | 20% | 30% | 40% | 50% |
|---|---|---|---|---|---|---|---|
| Initial peak strength (N) with loading end Compressed | | 1.1 | 1.4 | 2.2 | 2.7 | 3.4 | 4.9 |
| Presence or absence of breakage of cleaning part at compression test | | o | o | o | o | o | x |
| Presence or absence of bending of cleaning part at sensory teet | | x | x | o | o | o | o |
| Insertability evaluation (by 10 examiners) | Not insertable | 10 | 8 | 3 | 1 | 0 | 0 |
| | Insertable | 0 | 2 | 7 | 9 | 10 | 10 |
| Heat distortion temperature (° C.) | | 100 | 155 | 157 | 160 | 162 | 162 |

TABLE 1-continued

| Combination amount of glass fibers (weight %) | | 0% | 10% | 20% | 30% | 40% | 50% |
|---|---|---|---|---|---|---|---|
| Molding shrinkage ratio (%) of base part | Flow direction | 1.1 | 0.6 | 0.4 | 0.3 | 0.3 | 0.2 |
| | Orthogonal direction | 1.3 | 0.9 | 0.9 | 0.8 | 0.7 | 0.7 |
| Number of defective tools (unit) | | 3 | 1 | 0 | 0 | 0 | 0 |

\* Presence or absence of breakage at compression test: "o" indicates absence of breakage and "x" indicates presence of breakage
\* Presence or absence of bending at sensory test: "o" indicates absence of bending and "x" indicates presence of bending When the combination ratio of the glass fibers is equal to or more than 50 weight %, the core bases 12 were broken at the compression test, and when the combination ratio of the glass fibers is equal to or less than 10 weight %, the core bases 12 were bent at the use test to provide insufficient insertability of the cleaning parts 2. Accordingly, it is understood that the combination ratio of the glass fibers is preferably set to be equal to or more than 20 weight % and equal to or less than 40 weight %, in particular equal to or more than 30 weight. % and equal to or less than 40 weight %, for sufficient insertability of the cleaning parts 2. In addition, it is understood that, when the additive amount of the glass fibers is increased to 10 weight % or more, the base parts 10 are less prone to be thermally deformed and are increased in stability of molding dimensions. In particular, it is understood that, when the additive amount of the glass fibers is set at 20 weight % or more, charging failure of the base parts 10 into the second metal molds 40 and 41 can be completely prevented.

Next, an additional evaluation test on the interdental cleaning tools 1 will be described.

Five kinds of interdental cleaning tools 1 with different combination ratios of glass fibers were manufactured in such a manner that: synthetic resin materials were prepared by adding the glass fibers as the fiber material to polypropylene (PP) at combination ratios of 0 weight %, 10 weight %, 15 weight %, 20 weight %, and 30 weight %; these synthetic resin materials were used to five kinds of base parts 10; and cleaning flexible parts 21 made of a polystyrene-based elastomer were molded on core bases 12 of the five kinds of base parts 10. In addition, interdental cleaning tools 1 were manufactured in the same manner as the five kinds of interdental cleaning tools 1 except that, instead of the glass fibers, glass balls with a diameter of 0.086 mm (an average diameter of 0.086 mm and a standard deviation SD of 0.04 mm) were added by 40 weight %. Further, interdental cleaning tools 1 were manufactured in the same manner as the five kinds of interdental cleaning tools 1 except that, instead of the glass fibers, talc was added by 40 weight %. Moreover, two kinds of interdental cleaning tools 1 with different combination ratios of the glass fibers were manufactured in such a manner that: the glass fibers were added to polybutylene terephthalate (PBT) at the combination ratios of 0 weight % and 15 weight % to form synthetic resin materials; the synthetic resin materials were used to produce two kinds of base parts 10; and cleaning flexible parts 21 made of a polystyrene-based elastomer were molded on the core bases 12 of the two kinds of base parts 10. These interdental cleaning tools 1 were molded by the same first metal molds 30 and 31 and second metal molds 40 and 41 as used at the foregoing evaluation test.

Then, the nine kinds of interdental cleaning tools 1 were subjected to a horizontal bending test, a separating test, and a sensory test by ten examiners, in the following procedures. Table 2 shows results of the tests.

(Horizontal Bending Test)

Figure 14:
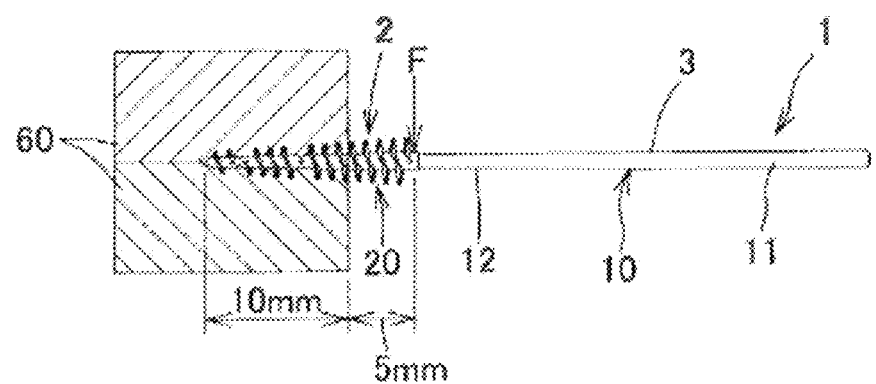
FIG. 14 is a diagram describing a method for conducting a horizontal bending test on the interdental cleaning tool.

As shown FIG. 14, each of the interdental cleaning tools 1 was sandwiched in an area of 10 mm from the leading end between a pair of fixing members 60 to support horizontally the interdental cleaning tool 1 in a cantilevered state. Then, force F was vertically applied at a rate 10 min/min to the interdental cleaning tool 1 at a position protruding outward from the fixing member 60 and separated by 5 mm from the fixing member 60 toward the base end, and maximum strength of the bent cleaning part 2 was measured.

(Separating Test)

Figure 15:
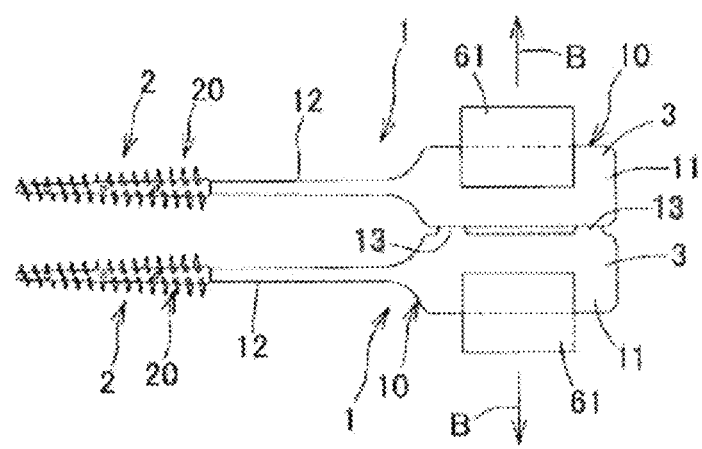
FIG. 15 is a diagram describing a method for conducting a separating test on the interdental cleaning tool.

As shown in FIG. 15, the two interdental cleaning tools 1 connected in parallel by the connection part 13 were held at the handles 3 by one pair of clamps 61. Then, the clamps 61 were separated from each other in a direction shown by arrow B at a tension ratio of 20 mm/min, and maximum strength of the two interdental cleaning tools 1 when being separated was measured.

(Sensory Test)

The ten examiners evaluated the interdental cleaning tools 1 for the presence or absence of bending of the cleaning parts 2, the presence or absence of breakage of the cleaning parts 2, and insertability of the cleaning parts 2 when the front teeth were cleaned and when the cheek teeth were cleaned. In Table 2, a rating "o" indicate that the cleaning part 2 was not bent or broken or the cleaning part 2 could be inserted into between teeth, and a rating "x" indicates that the cleaning part 2 was bent or broken or the cleaning part 2 could not be inserted into between teeth.

TABLE 2

| Base part resin | PP | | | | | | | PBT | |
|---|---|---|---|---|---|---|---|---|---|
| Additive | Glass fiber | | | | | Glass ball | Talc | Glass fiber | |
| Content rate (weight %) | 0% | 10% | 15% | 20% | 30% | 40% | 40% | 0% | 15% |
| Horizontal bending (N) | 0.05 | 0.09 | 0.12 | 0.13 | 0.17 | 0.06 | 0.09 | 0.11 | 0.19 |
| Separating (N) | 24.0 | 7.0 | 13.2 | 11.4 | 19.7 | 8.3 | 6.9 | 9.1 | 16.6 |
| Usability at front teeth | x | o | o | o | o | x | o | x | o |
| Usability at cheek teeth | x | x | o | o | o | x | x | o | o |

"o": The cleaning part is not bent or broken and the cleaning part can be inserted into between teeth
"x": The cleaning part is bent or broken and the cleaning part cannot be inserted into between teeth Next, other embodiments of the present invention in which the configuration of the metal mold device is partially modified, will be described. In the following description, the same members as those in the foregoing embodiment are given the same reference numerals as those in the foregoing embodiment, and detailed descriptions thereof are omitted.

Figure 16:
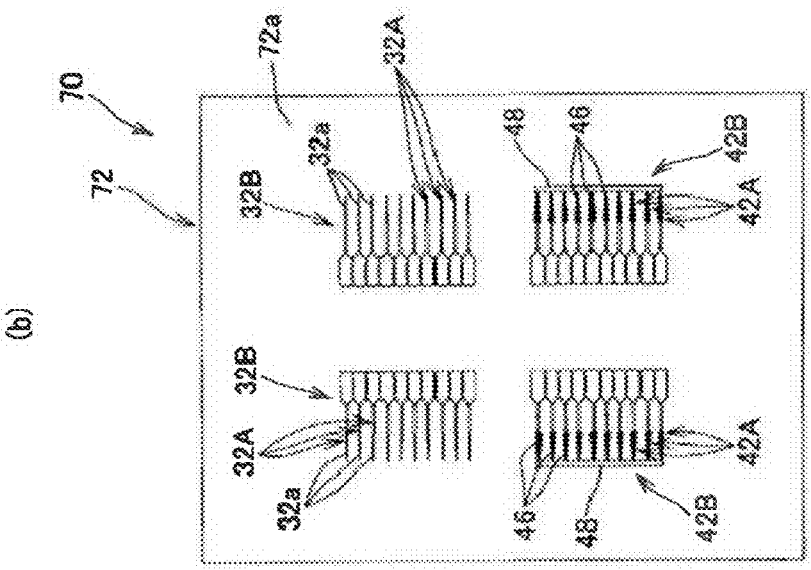
FIG. 16(a) is a front view of a matching surface of one metal mold in a metal mold device in another configuration.
FIG. 16(b) is a front view of a matching surface of the other metal mold in a metal mold device in another configuration.
Figure 16:
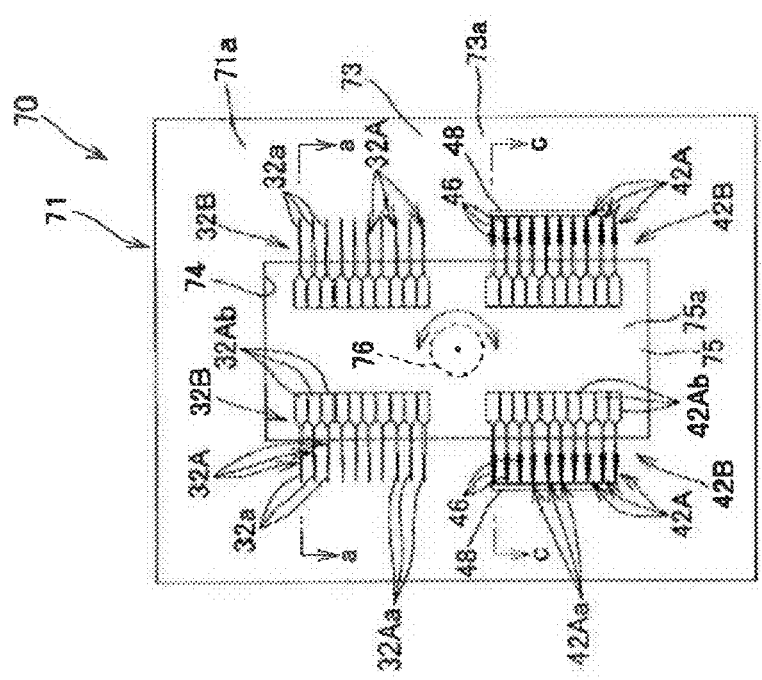
Figure 17:
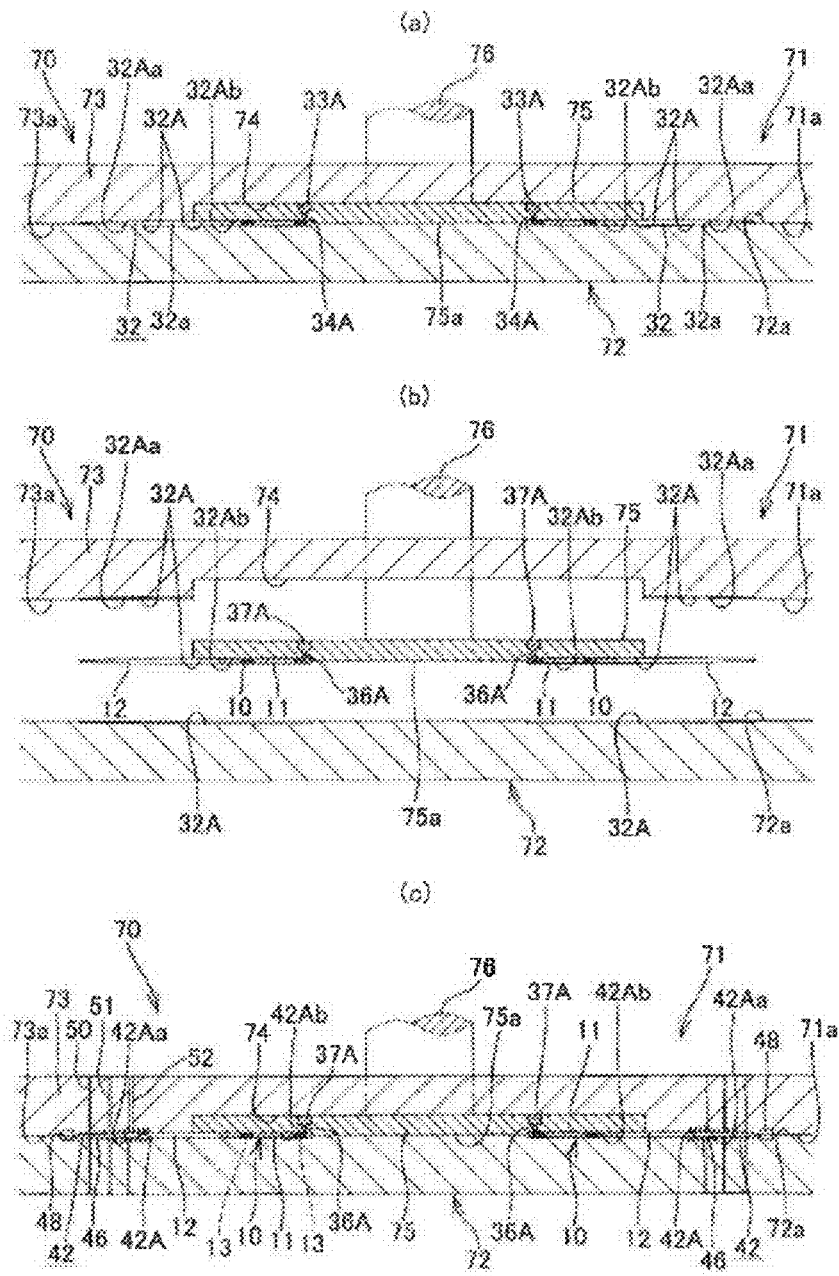
FIG. 17(a) is a cross section view of FIG. 16(a) taken along line a-a.
FIG. 17(b) is a cross section view of FIG. 16(a) in a mold-open state taken along line a-a.
FIG. 17(c) is across section view of FIG. 16(a) taken along line c-c.

(1) The metal mold device 70 shown in FIGS. 16 and 17 is formed by an integration of the metal mold device including the first metal molds 30 and 31 for producing the base parts 10 and the metal mold device including the second metal molds 40 and 41 for molding the flexible parts 20 in the foregoing embodiment. The metal mold device 70 includes a pair of metal molds 71 and 72 opposed to each other, and a rotation metal mold 75 in which the one metal mold 71 is fitted into a main metal mold 73 and a fitting concave 74 at a center of the main metal mold 73. The main metal mold 73 has on the center thereof a support shaft member 76 extending in a direction of mold opening/closing. The support shaft member 76 has a leading end connected to a center of the rotation metal mold 75, whereby the rotation metal mold 75 is supported at the main metal mold 73 via the support shaft member 76 so as to be capable of rotating and protruding from the fitting concave 74.

Two sets of base part molding section assemblies 32B each of which includes ten base part molding sections 32A almost horizontally aligned in parallel, are formed in mirror symmetry at upper parts of matching surfaces 71a and 72a of the metal molds 71 and 72, with the core base molding sections 32a positioned outside. Two sets of flexible part molding section assemblies 42B each of which includes ten flexible part molding sections 42A almost horizontally aligned in parallel, are formed in mirror symmetry at lower parts of matching surfaces 71a and 72a of the metal molds 71 and 72, with the cleaning flexible part molding sections 46 positioned outside. The numbers of the sets of base part molding section assemblies 32B and flexible part molding section assemblies 42B formed on the matching surfaces 71a and 72a can be arbitrarily set to be identical to each other.

The rotation metal mold 75 is square-shaped and configured such that both side edges of the rotation metal mold 75 pass through the longitudinal intermediate part of the core base molding sections 32a. Accordingly, the base part molding sections 32A formed at the upper part of the matching surface 71a of the metal mold 71 includes: leading end-side base part molding sections 32Aa for molding leading end-side portions of the core bases 12 at the upper part of the matching surface 73a of the main metal mold 73; and base end-side base part molding sections 32Ab for molding the entire handle bases 11 of the base parts 10 and base end-side portions of the core bases 12 at the upper part of the matching surface 75a of the rotation metal mold 75. The flexible part molding sections 42A formed at the lower part of the matching surface 71a of the metal mold 71 includes: leading end-side flexible part molding sections 42Aa including the cleaning flexible part molding section 46 for molding the cleaning flexible parts 21 on the core base 12 at the lower part of the matching surface 73a of the main metal mold 73; and base end-side flexible part molding sections 42Ab configured in the same manner as the base end-side base part molding sections 32Ab at the lower part of a matching surface 75a of the rotation metal mold 75. The base end-side base part molding sections 32Ab and the base end-side flexible part molding sections 42Ab are configured in the same manner. In this arrangement, the base end-side base part molding sections 32Ab are arranged at the upper part of the matching surface 75a of the rotation metal mold 75, and the base end-side flexible part molding sections 42Ab are arranged at the lower part of the matching surface 75a of the rotation metal mold 75.

The runners 33 are vertically formed on a back surface of the rotation metal mold 75 in correspondence with base ends of the ten base end-side base part molding sections 32Ab and ten base end-side flexible part molding sections 42Ab. The synthetic resin material is supplied through the runners 33 to the base end-side base part molding sections 32Ab from the gates 34 formed at the base ends of the base part molding section 32A.

To manufacture the interdental cleaning tools 1 using the metal mold device 70, first, two sets of primary molded articles 10A each of which includes the ten base parts 10 are molded by the upper two sets of base part molding section assemblies 32B in the rotation metal mold 75. Then, as shown in FIG. 17 (b), the metal molds 71 and 72 are opened to protrude the support shaft member 76 and eject the rotation metal mold 75 from the fitting concave 74, thereby separating the two sets of primary molded articles 10A from the main metal mold 73. At that time, each set of primary molded articles 10A is held at the rotation metal mold 75 so as not to fall off, by gate parts 38A and runner parts 37A made of a synthetic resin and molded by the gates 34A and the runners 33A.

Next, the rotation metal mold 75 is rotated 180° and fitted into the fitting concave 74 of the main metal mold 73 as shown in FIG. 17 (c). Then, the leading end-side portions of the core bases 12 in the two sets of primary molded articles 10A are set into the leading end-side flexible part molding sections 42Aa. In this state, the metal molds 71 and 72 are closed, and the base parts 11 are charged into the second molding spaces 42. Then, the hold pins 50 to 52 are protruded to position the core bases 12 at the center of the cleaning flexible part molding section 46. In this state, an elastomer is injected into the cleaning flexible part molding sections 46 from the leading end sides thereof via runners 48 to cover the core bases 12 by the cleaning flexible parts 21. Accordingly, it is possible to obtain two sets of interdental cleaning tool connected bodies 1A each of which ten interdental cleaning tools 1 are connected in parallel. At molding of the cleaning flexible parts 21 at the lower parts of the metal molds 71 and 72, the base parts 10 are also molded at the upper parts of the metal molds 71 and 72, which makes it possible to mold the two sets of interdental cleaning tool connected bodies 1A in sequence.

Figure 18:
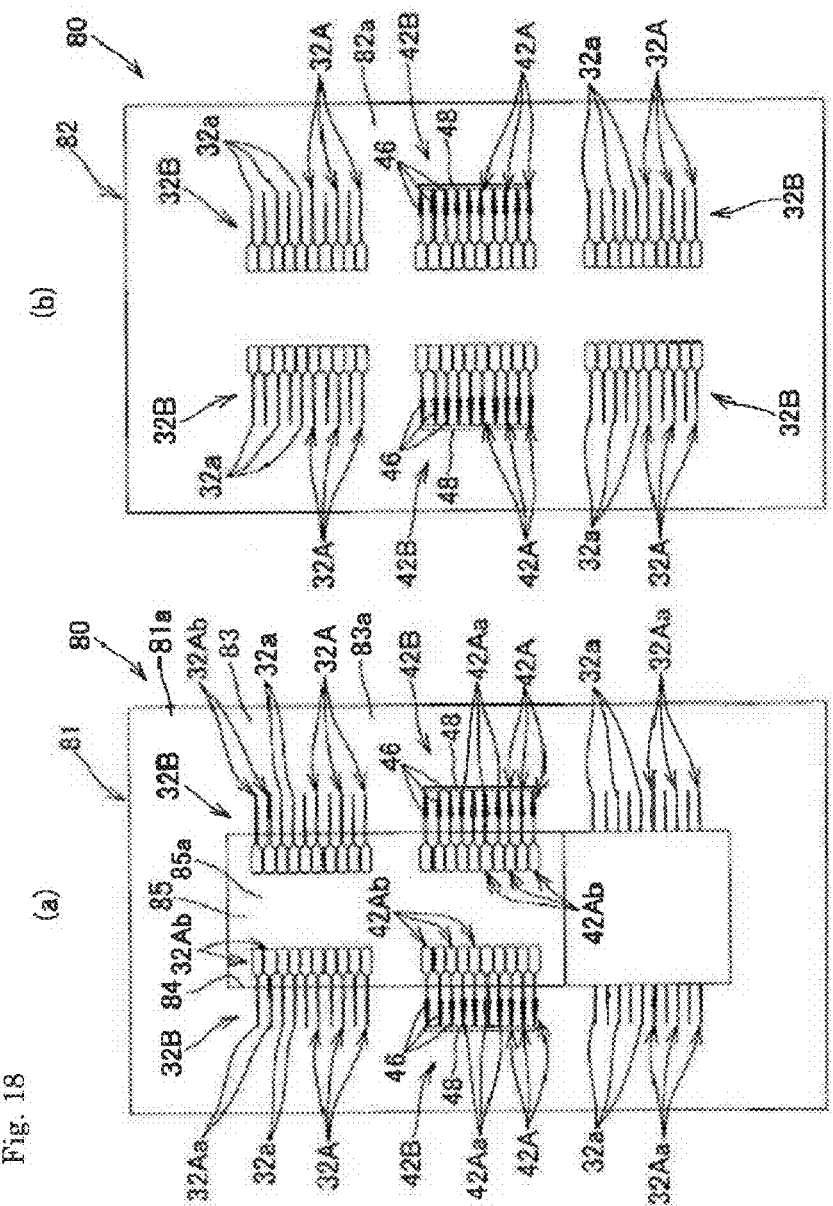
FIG. 18(a) is a front view of a matching surface of one metal mold in a metal mold device in another configuration.
FIG. 18(b) is a front view of a matching surface of the other metal mold in a metal mold device in another configuration.

(2) A metal mold device 80 shown in FIG. 18 is provided with one pair of metal molds 81 and 82 opposed to each other. The one metal mold 81 is formed by a main metal mold 83 and a slide metal mold 85 fitted into a fitting concave 84 at a center of the main metal mold 83. The slide metal mold 85 is supported an as to be capable of vertical position switching with respect to the main metal mold 83 and capable of protruding from the fitting concave 84. The slide metal mold 85 is configured in the same manner as the rotation metal mold 75 in the foregoing embodiment, except that the slide metal mold 85 is vertically slidable and capable of protruding from the fitting concave 84, unlike the rotation metal mold 75 in the foregoing embodiment that is supported at the main metal mold 73 so as to be capable of rotating and protruding from the fitting concave 74.

Two sets of base molding section assemblies 32B each of which includes ten base part molding sections 32A almost horizontally aligned in parallel, are formed at upper and lower parts of a matching surface 82a of the other metal mold 82, with the core base molding sections 32a positioned outside. Two sets of flexible part molding section assemblies 42B each of which includes ten flexible part molding sections 42A almost horizontally aligned in parallel, are formed at a heightwise intermediate part of the matching surface 82a of the other metal mold 82, with the cleaning flexible part molding sections 46 positioned outside.

Leading end-side base part molding sections 32Aa including leading end-side portions of the core base molding sections 32a, are formed at the upper and lower parts of a matching surface 83a of the main metal mold 83 on both sides of the fitting concave 84 of the one metal mold 81. Leading end-side flexible part molding sections 42Aa including the cleaning flexible part molding sections 46 are formed at a heightwise intermediate portion of the matching surface 83a of the main metal mold 83 on the both sides of the fitting concave 84. Two sets of base end-side base part molding sections 32Ab each of which includes the base end-side base part molding sections 32Ab, are formed in mirror symmetry at an upper part of a matching surface 85a of the slide metal mold 85. Two sets of base end-side flexible part molding sections 42Ab each of which includes ten base end-side flexible part molding sections 42Ab, are formed in mirror symmetry at a lower part of the matching surface 85a. The base end-side base part molding sections 32Ab and the base end-side flexible part molding sections 42Ab are configured in the same manner. When the slide metal mold 85 is positioned above the fitting concave 84, the base end-side base part molding parts 32Ab are positioned above the matching surface 85a, and the base end-side flexible part molding sections 42Ab are positioned under the matching surface 85a. When the slide metal mold 85 is positioned under the fitting concave 84, the base end-side flexible part molding sections 42Ab are positioned above the matching surface 85a, and the base end-side base part molding sections 32Ab are positioned under the matching surface 85a.

When the slide metal mold 85 is positioned above the fitting concave 84, the two sets of flexible part molding section assemblies 42B each of which includes ten flexible part molding sections 42A almost horizontally aligned in parallel, are formed in mirror symmetry at the heightwise intermediate portion of the matching surface 81a of the one metal mold 81, with the cleaning flexible part molding sections 46 positioned outside, and the two sets of base part molding section assemblies 32B each of which ten base part molding sections 32A almost horizontally aligned in parallel, are formed in mirror symmetry at the upper part of the matching surface 81a, with the core base molding sections 32a positioned outside. Meanwhile, when the slide metal mold 85 is positioned under the fitting concave 84, the two sets of flexible part molding section assemblies 42B are formed in mirror symmetry at the heightwise intermediate portion of the matching surface 81a of the one metal mold 81 as described above, and the two sets of base part molding section assemblies 32B are formed in mirror symmetry at the lower part of the matching surface 81a of the one metal mold 81 as described above.

To manufacture the interdental cleaning tools 1 using the metal mold device 80, the slide metal mold 85 is positioned above the fitting concave 84, for example, and two sets of primary molded articles 10A each of which includes ten base parts 10 are molded by the upper two sets of base part molding section assemblies 32B. Then, the metal molds 81 and 82 are opened, and the slide metal mold 85 is protruded from the fitting concave 84, thereby separating the two sets of primary molded articles 10A from the main metal mold 83. At that time, each set of primary molded articles 10A is held at the slide metal mold 85 by the gate parts 36A and the runner parts 37A made of a synthetic resin, as in the rotation metal mold 75.

Next, the slide metal mold 85 is moved to the underside of the fitting concave 84 of the main metal mold 83 and is fitted into the fitting concave 84. Then, leading end-side portions of the core bases 12 in the primary molded articles 10A are set into the leading end-side flexible part molding sections 42Aa positioned at the heightwise intermediate portion of the one metal mold 81. In this state, the two metal molds 81 and 82 are closed, and the base parts 11 are charged into the second molding spaces 42. Then, the hold pins 50 to 52 are protruded to position the core bases 12 at the central portions of the cleaning flexible part molding sections 46. In this state, an elastomer is injected into the cleaning flexible part molding sections 46 through the runners 48 from leading end sides thereof to cover the core bases 12 by the cleaning flexible parts 21. Accordingly, it is possible to obtain two sets of interdental cleaning tool connected bodies 1A each of which includes ten interdental cleaning tools 1 connected in parallel. In addition, at molding of the cleaning flexible parts 21 at the central part of the two metal molds 81 and 82, the base parts are also molded at the upper or lower part of the two metal molds 81 and 82, which makes it possible to mold the two sets of interdental cleaning tool connected bodies 1A in sequence.

(3) In an embodiment shown in FIGS. 19 and 20, first metal molds 90 and 91 for producing the base parts 10 and second metal molds 95 and 96 for molding the flexible parts 20 are provided. The one first metal mold 90 includes: a pair of first divided metal molds 90A and 90B that can move between a combined state shown by solid lines and a separated state shown by virtual lines in the drawings; and a transfer metal mold 100 fitted into a fitting concave 93 at a central part formed by combining the two first divided metal molds 90A and 90B. The one second metal mold 95 includes: a pair of second divided metal molds 95A and 95B that can move between a combined state shown by solid lines and a separated state shown by virtual lines in the drawings; and a transfer metal mold 100 fitted into a fitting concave 97 at a central portion formed by combining the two second divided metal molds 95A and 95B. The transfer metal molds 100 are configured in the same manner as the rotation metal mold 75 except that the transfer metal molds 100 are provided so as to be capable of transfer across the first divided metal molds 90A and 90B and the second divided metal molds 95A and 95B, unlike in the foregoing embodiment in which the rotation metal mold 75 is supported at the main metal mold 73 so as to be capable of rotating and protruding from the fitting concave 74.

Four sets of base part molding section assemblies 32B each of which includes ten base part molding sections 32 almost horizontally aligned in parallel, are formed on matching surfaces of the first metal molds 90 and 91. Four sets of flexible part molding section assemblies 42B each of which includes ten flexible part molding sections 42A almost horizontally aligned in parallel, are formed on matching surfaces of the second metal molds 95 and 96.

To mold the interdental cleaning tools 1 using the first metal molds 90 and 91 and the second metal mold 95 and 96, first, the first metal molds 90 and 91 are closed to mold four sets of primary molded articles 10A each of which includes ten base parts 10 by the four sets of base part molding section assemblies 32B. Then, the two first metal molds 90 and 91 are opened, and the first divided metal molds 90A and 90B are separated to eject the four sets of primary molded articles 10A from the first divided metal molds 90A and 90B.

At that time, each set of primary molded articles 10A is held at the transfer metal mold 100 by the gate parts 36A and the runner parts 37A made of a synthetic resin, as in the rotation metal mold 75.

Next, the transfer metal mold 100 is transferred to between the second divided metal molds 95A and 95B, and the second divided metal molds 95A and 95B are combined to integrate the second divided metal molds 95A and 95B with the transfer metal mold 100. After that, the second metal molds 95 and 96 are closed, and the four sets of primary molded articles 10A are set into the four sets of flexible part molded section assemblies 42B, and the base parts 11 are charged into the second molded spaces 42. Then, the hold pins 50 to 52 are protruded to position the core bases 12 at the central portions of the cleaning flexible part molding sections 46. In this state, an elastomer is injected into the cleaning flexible part molding sections 46 through the runners 48 from the leading end sides thereof to cover the core bases 12 by the cleaning flexible parts 21. Accordingly, it is possible to obtain four sets of interdental cleaning tool connected bodies 1A each of which includes ten interdental cleaning tools 1 connected in parallel. When the two or more transfer metal molds 100 are provided and cyclically transferred between the first metal molds 90 and 91 and the second metal molds 95 and 96, it is possible to mold the four sets of interdental cleaning tool connected bodies 1A in sequence.

The embodiments of the invention are described above. However, the invention is not limited to the foregoing embodiments. As a matter of the course, the configurations of the embodiments can be modified without departing from the gist of the present invention.

REFERENCE SIGNS LIST

1 Interdental cleaning tool
1A Interdental cleaning tool connected body
2 Cleaning part
3 Handle part
10 Base part
11 Handle base
11a Side surface
12 Core base
12a Exposure part
12b Core body
13 Connection part
13a First boundary part.
13b Second boundary part
13c Oblique side
13d Oblique side
20 Flexible part
21 Cleaning flexible part
21a Covered part
21b Protrusion
10A Primary molded article
30 First metal mold
31 First metal mold
32 First molding space
32a Core base molding section
32b Handle base Molding section
33 Runner
34 Gate
35 Connection part molding section
35a First boundary section
35b Second boundary section
32c Oblique side
32d Oblique side
36 Gate part
37 Runner part
40 Second metal mold
40a Matching surface
41 Second metal mold
41a Matching surface
42 Second molding space
43 Fitting space
44 Fitting space
45 Fitting space
46 Cleaning flexible part molding section
46a Leading end
47 Gate
48 Runner
50 Leading end-side hold pin
51 Middle portion hold pin
52 Base end-side hold pin
55 Runner part
56 Gate part
60 Fixing member
61 Clamp
32A Base part molding section
32Aa Leading end-side base part molding section
32Ab Base end-side base part molding section
32B Base part molding section assembly
33A Runner
34A Gate
36A Gate part
37A Runner part
42A Flexible part molding section
42Aa Leading end-side flexible part molding section
42Ab Base end-side flexible part molding section
42B Flexible part mottling section assembly
70 Metal mold device
71 Metal mold
71a Matching surface
72 Metal mold
72a Matching surface
73 Main metal mold
73a Matching surface
74 Fitting concave
75 Rotation metal mold
75a Matching surface
76 Support shaft member
80 Metal Mold device
81 Metal mold
81a Marching surface
82 Metal mold
82a Matching surface
83 Main metal mold
83a Matching surface
84 Fitting concave
85 Slick metal mold
85a Matching surface
90 Metal mold
91 Metal mold
90A Divided metal mold
90B Divided metal mold
92 Metal mid
93 Fitting concave
95 Metal mold
95A Divided metal mold.
95B Divided metal mold.
96 Metal mold
97 Fitting concave
100 Transfer metal mold

The invention claimed is:

1. A method for manufacturing interdental cleaning tools, each interdental cleaning tool comprising: a base part made of a synthetic resin, the base part having a handle base and an elongated shaft-like core base connected to a leading end of the handle base; and a flexible part made of an elastomer and covering at least a portion of the base part, the flexible part having at least a cleaning flexible part covering the core base, the handle base constituting a handle part, and the core base and the cleaning flexible part constituting an interdental cleaning part, wherein the method comprises:

a core base part molding step of: providing a first metal mold for molding the base parts with a plurality of first molding spaces aligned in parallel and including core base molding sections and handle base molding sections; providing the first metal mold with connection part molding sections to communicate with adjacent handle base molding sections; supplying a synthetic resin material with a fiber material at a time to the plurality of first molding spaces from gates opened to the first molding spaces at base end sides of the first molding spaces opposite to the core base molding sections; and forming a plurality of core base parts at a time such that the base parts are connected to each other in parallel by connection parts molded at the connection part molding sections, and a flexible part molding step of: transferring the connected core base parts molded and connected to each other in the base part molding step to a second metal mold for molding the flexible parts; setting at least portions of the core bases of the connected base parts into a plurality of second molding spaces in the second metal mold for molding the flexible parts; holding the core bases at two or more longitudinal portions including at leading ends and base ends of the core bases, at approximately centers of cleaning flexible part molding sections of the second mold and by at least two pairs of hold pins of the second mold, each pair of the hold pins including two pins that are opposed to each other and that protrude within the cleaning flexible part molding sections so as to be approximately perpendicular to matching surfaces of the second metal mold from which the pins protrude; and charging an elastomer material into the second molding spaces over the held core bases such that the elastomer material is supplied from leading end sides to base end sides of the cleaning flexible part molding sections, wherein:

a first pair of hold pins of the at least two pairs of hold pins holds the leading end of the connected core base parts with each pin of the first pair of hold pins having a cross sectional area in contact with each core base part of 0.03 to 0.3 mm$^2$, the first pair of hold pins is arranged at positions where leading ends of the first pair of pins hold the core base parts within 3 mm from the leading end sides to the base end sides of the cleaning flexible part molding sections, a second pair of hold pins of the at least two pairs of hold pins holds the base end of the connected core base parts with each pin of the second pair of hold pins having a cross sectional area in contact with each core base part of 0.1 to 1.1 mm$^2$, the second pair of hold pins is arranged at positions where leading ends of the second pair of pins hold the core base parts within 6 mm from the base end sides to leading end sides of the cleaning flexible part molding sections, and the positioning and cross sectional areas of the first and second pair of hold pins contributes to centering the core base parts stably in the flexible part molding sections while minimizing a flow resistance to the elastomer material around at least the first and second pairs of holding pins.

2. The method for manufacturing interdental cleaning tools according to claim 1, wherein
the connection part molding sections are elongated along a length of the handle base molding sections and are thinner with increasing proximity to a first boundary section of two boundary sections between the connection part molding section and the handle base molding sections on both sides of the connection part molding section.

3. The method for manufacturing interdental cleaning tools according to claim 1, wherein, of two boundary sections between the connection part molding section and the handle base molding sections on both sides of the connection part molding section, the length of first boundary section along the length of the handle base molding section is smaller than the length of second boundary part.

4. The method for manufacturing interdental cleaning tools according to claim 1, wherein two or more connection part molding sections are arranged at intervals along the length of each of the handle base molding sections.

5. The method for manufacturing interdental cleaning tools according to claim 1, wherein
the fiber material comprises glass fiber, and
a combination ratio of the glass fiber to the synthetic resin material is 12 weight % or more and 35 weight % or less.

6. The method for manufacturing interdental cleaning tools according to claim 1, wherein the synthetic resin material is polypropylene (PP), polybutylene terephthalate (PBT), or polyamide.

7. The method for manufacturing interdental cleaning tools according to claim 1, wherein the hold pins are provided to freely appear at the cleaning flexible part molding section.

8. The method for manufacturing interdental cleaning tools according to claim 1, wherein the synthetic resin material for forming the base part and the elastomer material for forming the flexible part are compatible with each other.

9. The method for manufacturing interdental cleaning tools according to claim 1, wherein the elastomer material is a styrene-based elastomer material.

10. The method for manufacturing interdental cleaning tools according to claim 1, wherein a core main body of each core base part has a diameter of 0.4 to 0.6 mm at a leading end thereof and a diameter of 0.8 to 2.0 mm at a base end thereof.

11. The method for manufacturing interdental cleaning tools according to claim 1, wherein the positioning and cross sectional areas of the first and second pair of holding pins contributes to a prevention of Karman vortex generated near the first and second pairs of hold pins during the molding of the elastomer material.

* * * * *